United States Patent
Milenkovic et al.

(10) Patent No.: US 12,380,337 B2
(45) Date of Patent: Aug. 5, 2025

(54) CODED TRACE RECONSTRUCTION

(71) Applicant: The Board of Trustees of the University of Illinois, Urbana, IL (US)

(72) Inventors: Olgica Milenkovic, Urbana, IL (US); Ryan Gabrys, San Diego, CA (US); João Ribeiro, London (GB); Mahdi Cheraghchi Bashi Astaneh, London (GB)

(73) Assignees: the Board of Trustees of the University of Illinois, Urbana, IL (US); Imperial College Innovations Limited, London (GB)

( * ) Notice: Subject to any disclaimer, the term of this patent is extended or adjusted under 35 U.S.C. 154(b) by 950 days.

(21) Appl. No.: 17/069,247

(22) Filed: Oct. 13, 2020

(65) Prior Publication Data
US 2021/0125079 A1     Apr. 29, 2021

Related U.S. Application Data

(60) Provisional application No. 62/925,332, filed on Oct. 24, 2019.

(51) Int. Cl.
| | | |
|---|---|---|
| *G01N 33/48* | (2006.01) | |
| *C12N 15/10* | (2006.01) | |
| *C12Q 1/6869* | (2018.01) | |
| *G01N 33/50* | (2006.01) | |
| *G06N 3/123* | (2023.01) | |
| *G06N 3/126* | (2023.01) | |

(52) U.S. Cl.
CPC ......... *G06N 3/123* (2013.01); *C12N 15/1065* (2013.01); *C12Q 1/6869* (2013.01); *G06N 3/126* (2013.01)

(58) Field of Classification Search
CPC ............................... G06N 3/123; G06N 3/126
USPC .......................................................... 702/19
See application file for complete search history.

(56) References Cited

U.S. PATENT DOCUMENTS

| | | | |
|---|---|---|---|
| 6,223,128 | B1 | 4/2001 | Allex |
| 7,227,900 | B2 | 6/2007 | Porter |
| 9,996,778 | B2 | 6/2018 | Church |
| 10,370,246 | B1 | 8/2019 | Milenkovic |
| 10,566,077 | B1 | 2/2020 | Milenkovic |
| 11,538,554 | B1 | 12/2022 | Milenkovic |
| 2004/0001371 | A1 | 1/2004 | Mansuripur |
| 2005/0053968 | A1 | 3/2005 | Bharadwaj |
| 2015/0261664 | A1 | 9/2015 | Goldman |
| 2017/0141793 | A1 | 5/2017 | Strauss |
| 2018/0127804 | A1 | 5/2018 | Dean |
| 2020/0004926 | A1 | 1/2020 | Strauss |
| 2020/0035331 | A1 | 1/2020 | Milenkovic |
| 2020/0185057 | A1 | 6/2020 | Leake |
| 2021/0074380 | A1* | 3/2021 | Yekhanin .......... G06F 16/90344 |
| 2021/0098081 | A1 | 4/2021 | Yekhanin |
| 2021/0103824 | A1 | 4/2021 | Milenkovic |
| 2021/0191970 | A1 | 6/2021 | Pan |

FOREIGN PATENT DOCUMENTS

WO    2008087042 A1    7/2008

OTHER PUBLICATIONS

Shendure, Jay, et al. "DNA sequencing at 40: past, present and future." Nature 550.7676 (2017): 345-353. (Year: 2017).*
Cheraghchi, Mahdi, et al. "Coded Trace Reconstruction." arXiv preprint arXiv:1903.09992 (2019). (Year: 2019).*
Illumina Sequencing "Sequencing Platforms." Sequencing Platforms | Illumina NGS Platforms, www.illumina.com/systems/sequencing-platforms.html. Accessed Sep. 21, 2023. (Year: 2023).*
Rose et al. A statistical mechanical treatment of error in the annealing biostep of DNA computation. Proceedings of the Genetic and Evolutionary Computation Conference. Volume 2. San Francisco: Morgan Kauffman, 6 pages. (Year: 1999).*
Deaton et al. Reliability and efficiency of a DNA-based computation. Physical Review Letters, vol. 80, pp. 417-420. (Year: 1998).*
Craig et al. Ordering of cosmid clones covering the Herpes simplex virus type I (Hsv-I) genome: a test case for fingerprinting by hybridisation. Nucleic Acids Research, vol. 18, pp. 2653-2660. (Year: 1990).*
Yazdi et al., "Portable and Error-Free DNA-Based Data Storage," Scientific Reports, www.nature.com/scientificreports, 2017, 6 pages, vol. 7, Article No. 5011.
Smith, et al.; "Removal of polymerase-produced mutant sequences from pcr products,"; Proceedings of the National Academy of Sciences, vol. 94, No. 13, pp. 6847-6850 (1997).
Song, et al., "Sequence-subset distance and coding for error control in DNA-based data storage," arXiv e-prints, p. arXiv:1809.05821, Sep. 2018.
Srinivasavaradhan, et al., "On maximum likelihood reconstruction over multiple deletion channels," in 2018 IEEE International Symposium on Information Theory (ISIT), Jun. 2018, pp. 436-440.
Stanley; "Enumerative combinatorics."; Cambridge university press; vol. 1. (2011).

(Continued)

*Primary Examiner* — Russell S Negin
(74) *Attorney, Agent, or Firm* — McDonnell Boehnen Hulbert & Berghoff LLP

(57) ABSTRACT

The present disclosure provides systems and methods that relate to storing encoded information in, and reading the encoded information from, nucleotide sequences. An example method includes receiving, at a DNA readout system, a nucleotide sequence. The method also includes reading the nucleotide sequence based on an alphabet consisting of {adenine (A), cytosine (C), guanine (G), and thymine (T)}. The method further includes determining positions of unique markers between a plurality of encoded blocks in the nucleotide sequence. The method yet further includes decoding each encoded block of the plurality of encoded blocks according to an inner code, so as to form a plurality of decoded blocks. The method also includes appending the decoded blocks to one another to provide a decoded message with message length n bits.

12 Claims, 4 Drawing Sheets

(56) References Cited

OTHER PUBLICATIONS

Stemmer, et al.; "Single-step assembly of a gene and entire plasmid from large numbers of oligodeoxyribonucleotides,"; Gene, vol. 164, No. 1, pp. 49-53 (1995).
Stojanovic, et al.; "A deoxyribozyme-based molecular automaton,"; Nature Biotechnology vol. 21, pp. 1069-1074 (2003).
Svanstrom, et al.; "Bounds and constructions for ternary constant-composition codes,"; IEEE Trans. Inform. Theory, vol. 48, No. 1, pp. 101-111 (Jan. 2002).
Tabatabaei et al., "DNA punch cards for storing data on native DNA sequences via enzymatic nicking". Nature Communications (2020) 11:17:1742 https://doi.org/10.1038/ s41467-020-15588-z www.nature.com/naturecommunications.
Tabatabaei Yazdi, et al., "Mutually uncorrelated primers for DNA-based data storage," IEEE Transactions on Information Theory, vol. 64, No. 9, pp. 6283-6296, Sep. 2018.
Tabatabaei Yazdi, S. M. H., et al.; "DNA-Based Storage: Trends and Methods"; arXiv:1507.01611; published to arxiv.org on Jul. 6, 2015.
Tabatabaei Yazdi, S. M. H., et al.; "A Rewritable, Random-Access DNA-Based Storage System."; Sci. Rep. 5, 14138; doi: 10.1038/srep14138 (Sep. 18, 2015).
Tabatabaei Yazdi, S. M. H., et al.; "Weakly Mutually Uncorrelated Codes"; arXiv: 1601.08176; Published to arxiv.org on Jan. 29, 2016.
Tabatabaei Yazdi, S. M. H., et al.; Supplementary Information for "A Rewritable, Random-Access DNA-Based Storage System"; Sci. Rep. 5, 14138 (Sep. 18, 2015).
Tal, I., et al.; "How to construct polar codes,"; IEEE Trans. on Info. Theory, vol. 59, No. 10, pp. 6562-6582 (Sep. 2013).
Tan, et al.; "Sets represented as the length-n factors of a word,"; in Combinatorics on Words; Springer; pp. 250-261 (2013).
Tavares; "A study of synchronization techniques for binary cyclic codes,"; Ph.D. dissertation, Thesis (Ph. D.)—McGill University (1968).
Tian, et al.; "Accurate multiplex gene synthesis from programmable DNA microchips,"; Nature, vol. 432, No. 7020, pp. 1050-1054 (2004).
Tian, et al.; "Advancing high-throughput gene synthesis technology,"; Molecular BioSystems, vol. 5, No. 7, pp. 714-722 (2009).
Till, et al.; "Mismatch cleavage by single-strand specific nucleases,"; Nucleic Acids Research, vol. 32, No. 8, pp. 2632-2641 (2004).
Tomasi and Manduchi, "Bilateral Filtering for Gray and Color Images", Proceeding of the 1998 IEEE International Conference on Computer Vision, Bombay, India, 8 pages.
Tsaftaris, et al.; "DNA computing from a signal processing viewpoint,"; IEEE Signal Processing Magazine, pp. 100-106 (Sep. 2004).
Tzeng, et al.; "On extending Goppa codes to cyclic codes," IEEE Trans. Inform. Theory, vol. IT-21, pp. 712-716 (Nov. 1975).
Ukkonen; "Approximate string-matching with q-grams and maximal matches,"; Theoretical computer science, vol. 92, No. 1, pp. 191-211 (1992).
Varshamov; "A class of codes for asymmetric channels and a problem from the additive theory of numbers,"; IEEE Trans. Inform. Theory, vol. 19, No. 1, pp. 92-95 (1973).
Vilenchik; "Endogenous DNA double-strand breaks: production, fidelity of repair, and induction of cancer,"; Proceedings of the National Academy of Sciences, vol. 100, No. 22, pp. 12871-12876 (2003).
Wan, et al.; "Error removal in microchip-synthesized DNA using immobilized muts,"; Nucleic acids research, p. gku405 (2014).
Waterston, et al.; "Initial sequencing and comparative analysis of the mouse genome,"; Nature, vol. 420, No. 6915, pp. 520-562 (Dec. 2002).
Wheeler, et al.; "The complete genome of an individual by massively parallel DNA sequencing,"; Nature, vol. 452, No. 7189, pp. 872-876 (Apr. 2008).
Winfree, "DNA computing by self-assembly," The Bridge, vol. 33, No. 4, pp. 31-38 (2003); Also available online at http://www.dna.caltech.edu/Papers/FOE 2003 final.pdf.
Wolf; "On codes derivable from the tensor product of check matrices,"; IEEE Transactions on Information Theory, vol. 11, No. 2, pp. 281-284 (1965).
Wood; "Applying error correcting codes to DNA computing (Abstract)"; Proceedings of the 4th DIMACS International Meeting on DNA Based Computing, pp. 109-110 (1998).
Ye et al, Primer-Blast: A tool to design target-specific primers for polymerase chain reaction BMC Bioinformatics, vol. 13, article 134 (2012).
Zerbino, et al.; "Velvet: algorithms for de novo short read assembly using de Bruijn graphs,"; Genome Res., vol. 18, No. 5, pp. 821-829 (May 2008).
Zhirnov et al., Nucleic Acid Memory, Nat. Mater. Apr. 2016; 15(4):366-370. doi: 10.1038/nmat4594.
Zuker; "Mfold web server for nucleic acid folding and hybridization prediction,"; Nucleic Acids Res., vol. 31, No. 13, pp. 3406-3415 (2003) Web access at http://www.bioinfo.rpi.edu/«zukerm/rna/.
Milenkovic, et al, "Exabytes in a test tube," IEEE Spectrum, vol. 55, No. 5, pp. 40-45, 2018.
Milenkovic, et al.; "DNA codes that avoid secondary structures," Proc. IEEE Int. Symp. Inform. Theory (ISIT'05), Adelaide, Australia, pp. 288-292 (Sep. 2005).
Milenkovic, et al.; "On the design of codes for DNA computing"; Coding and Cryptography International Workshop, Revised Selected Papers, pp. 100-119 (Mar. 14-18, 2005).
Milenkovic, O., et al.; "On the design of codes for DNA computing."; In Coding and Cryptography, 100-119 (Springer, 2006).
Milenkovic; "On the generalized Hamming weight enumerators and coset weight distributions of even isodual codes,"; Proceedings of the 2001 IEEE International Symposium on Information Theory (Jun. 29, 2001).
Mneimneh; "Computational Biology Lecture 20: RNA secondary structures,"; available online at engr.smu.edu/«saad/courses/cse8354/lectures/lecture20.pdf.
Moon, et al., "Analysis of the clustering properties of the Hilbert space-filling curve," in IEEE Transactions on Knowledge and Data Engineering, vol. 13, No. 1, pp. 124-141, Jan.-Feb. 2001, doi: 10.1109/69.908985.
Morita, H., et al.; "On the construction of maximal prefix-synchronized codes."; Information Theory, IEEE Transactions on 42, 2158-2166 (1996).
Nakamura, et al.; "Sequence-specific error profile of Illumina sequencers,"; Nucleic acids research; p. gkr344, (2011).
Nazarov et al., "Trace reconstruction with exp(O(n1/3) samples," in Proceedings of the 49th Annual ACM SIGACT Symposium on Theory of Computing (STOC), 2017, pp. 1042-1046.
Nazeri et al., "EdgeConnect: Generative Image Inpainting with Adversarial Edge Learning", https://github.com/knazeri/edge-connect; pp. 1-17.
Notice of Allowance, U.S. Appl. No. 15/356,118, mailed Sep. 16, 2019.
Nussinov, et al.; "Fast algorithms for predicting the secondary structure of single stranded RNA,"; Proc. Natl. Acad. Sci. USA, vol. 77, No. 11, pp. 6309-6313 (1980).
Nuwaysir, et al.; "Gene expression analysis using oligonucleotide arrays produced by maskless photolithography,"; Genome research, vol. 12, No. 11, pp. 1749-1755 (2002).
Office Action, U.S. Appl. No. 15/356,118, mailed May 3, 2019.
Office Action, U.S. Appl. No. 15/356,118, mailed Jul. 19 2019.
Office Action, U.S. Appl. No. 17/102,143, mailed Feb. 17, 2023.
Oleykowski, et al.; "Mutation detection using a novel plant endonuclease,"; Nucleic acids research, vol. 26, No. 20, pp. 4597-4602 (1998).
Organick, et al., "Random access in large-scale DNA data storage," Nature biotechnology, vol. 36, No. 3, p. 242, 2018.
Packer, H.; "CRISPR and Cas9 for flexible genome editing."; Technical report. (2014); Available at: www.idtdna.com/pages/products/genes/gblocks-gene-fragments/decoded-articles/decoded/2013/12/13/crispr-and-cas9-for-flexible-genome-editing. (Accessed: Jan. 1, 2015).

(56) References Cited

OTHER PUBLICATIONS

Paluncic, et al.; "A note on non-binary multiple insertion/deletion correcting codes," in IEEE Information Theory Workshop (2011).
Pease, et al.; "Light-generated oligonucleotide arrays for rapid DNA sequence analysis,"; Proceedings of the National Academy of Sciences, vol. 91, No. 11, pp. 5022-5026 (1994).
Peres et al, "Average-case reconstruction for the deletion channel: subpolynomially many traces suffice," arXiv e-prints, p. arXiv:1708.00854, Aug. 2017.
Pevzner, et al.; "An Eulerian path approach to DNA fragment assembly,"; Proc. Natl. Acad. Sci. U.S.A., vol. 98, No. 17, pp. 9748-9753 (Aug. 2001).
Pevzner, et al.; "Towards DNA sequencing chips,"; in Mathematical Foundations of Computer Science 1994. Springer, pp. 143-158 (1994).
Quan, et al.; "Parallel on-chip gene synthesis and application to optimization of protein expression,"; Nature biotechnology, vol. 29, No. 5, pp. 449-452 (2011).
Reed, et al.; "Polynomial codes over certain finite fields,"; Journal of the society for industrial and applied mathematics, vol. 8, No. 2, pp. 300-304 (1960).
Reese; "Oligo-and poly-nucleotides: 50 years of chemical synthesis,"; Organic & biomolecular chemistry, vol. 3, No. 21, pp. 3851-3868 (2005).
Richardson, et al.; "The capacity of low-density parity-check codes under message-passing decoding,"; IEEE Trans. on Info. Theory, vol. 47, No. 2, pp. 599-618 (Aug. 2002).
Ross, M. G., et al.; "Characterizing and measuring bias in sequence data."; Genome Biol 14, R51 (2013).
Rouillard, J.-M., et al.; "Oligoarray 2.0: design of oligonucleotide probes for DNA microarrays using a thermodynamic approach."; Nucleic acids research 31, 3057-3062 (2003).
Roy, et al.; "Synthesis of dna/rna and their analogs via phosphoramidite and h-phosphonate chemistries,"; Molecules, vol. 18, No. 11, pp. 14 268-14 284 (2013).
Ruskey, et al.; "De Bruijn sequences for fixed-weight binary strings,"; SIAM Journal on Discrete Mathematics, vol. 26, No. 2, pp. 605-617 (2012).
Rykov, et al.; "DNA sequences and quaternary cyclic codes," Proc. IEEE Int. Symp. Inform. Theory (ISIT'01), Washington DC, p. 248 (Jun. 2001).
Saaem, et al.; "Error correction of microchip synthesized genes using surveyor nuclease,"; Nucleic acids research, p. gkr887 (2011).
Sala, et al.; "Exact reconstruction from insertions in synchronization codes,"; arXiv preprint, arXiv:1604.03000 (2016).
Sanger, et al.; "DNA sequencing with chainterminating inhibitors,"; Proc. Natl. Acad. Sci. U.S.A., vol. 74, No. 12, pp. 5463-5467 (Dec. 1977).
Schoeny, et al.; "Codes for correcting a burst of deletions or insertions,"; arXiv preprint, arXiv:1602.06820 (2016).
Schouhamer Immink et al., "Very efficient balanced codes," IEEE Journal on Selected Areas in Communications, vol. 28, No. 2, pp. 188-192, Feb. 2010.
Schulman; "Asymptotically good codes correcting insertions, deletions, and transpositions,"; IEEE transactions on information theory, vol. 45, No. 7, pp. 2552-2557 (1999).
Schuster, S. C.; "Next-generation sequencing transforms today's biology."; Nature methods 5, 16-18 (2008).
Schwartz, et al.; "Accurate gene synthesis with tag-directed retrieval of sequence-verified dna molecules,"; Nature methods, vol. 9, No. 9, pp. 913-915 (2012).
Shendure et al, Next-generation DNA sequencing Nature Biotechnology vol. 26, pp. 1135-1145 (2008).
Shinkar, et al., "Clustering-correcting codes," arXiv e-prints, p. arXiv:1903.04122, Mar. 2019.
Shomorony et al., "Capacity results for the noisy shuffling channel," arXiv e-prints, p. arXiv:1902.10832, Feb. 2019.
Simpson, et al.; "ABySS: a parallel assembler for short read sequence data,"; Genome Res., vol. 19, No. 6, pp. 1117-1123 (Jun. 2009).
Simpson, et al.; "Efficient de novo assembly of large genomes using compressed data structures,"; Genome Res., vol. 22, No. 3, pp. 549-556 (Mar. 2012).
Singh-Gasson, et al.; "Maskless fabrication of light-directed oligonucleotide microarrays using a digital micromirror array,"; Nature biotechnology, vol. 17, No. 10, pp. 974-978 (1999).
Sinha, et al.; "Polymer support oligonucleotide synthesis xviii1. 2): use of cyanoethyi-n, ndialkylamino-/n-morpholino phosphoramidite of deoxynucleosides for the synthesis of dna fragments simplifying deprotection and isolation of the final product," Nucleic Acids Research, vol. 12, No. 11, pp. 4539-4557 (1984).
Sloane; "On single-deletion-correcting codes,"; Codes and Designs, de Gruyter, Berlin, pp. 273-291 (2002).
"gBlocks (TM) Gene Fragments Cloning Protocols"; http://www.idtdna.com/pages/docs/synthetic-biology/gblocks-user-guide.pdf; retrieved Nov. 15, 2016.
"Overlap Extension Polymerase Chain Reaction"—Wikipedia article; https://en.wikipedia.org/wiki/Overlap_extension_polymerase_chain_reaction; retrieved Nov. 15, 2016.
Abroshan, et al., "Coding for deletion channels with multiple traces," arXiv e-prints, p. arXiv:1905.08197, May 2019.
Abualrub, et al.; "Construction of cyclic codes over GF(4) for DNA computing"; Journal of the Franklin Institute, 343, pp. 448-457 (2006).
Acharya, et al.; "On reconstructing a string from its substring compositions,"; Proc. IEEE Intl. Symp. Inform. Theory; IEEE; pp. 1238-1242 (2010).
Acharya, et al.; "Quadratic-backtracking algorithm for string reconstruction from substring compositions,"; Proc. IEEE Intl. Symp. Inform. Theory; IEEE; pp. 1296-1300 (2014).
Adleman; "Molecular computation of solutions to combinatorial problems,"; Science, vol. 266, pp. 1021-1024 (Nov. 1994).
Ahuja, et al.; "Network flows: theory, algorithms, and applications."; Prentice Hall (1993).
Alderson, et al.; "On maximum Lee distance codes,"; J. of Discrete Mathematics (2013).
Alon, et al., "Simple constructions of almost k-wise independent random variables," Random Structures & Algorithms, vol. 3, No. 3, pp. 289-304, 1992.
Astola; "The Theory of Lee-codes,"; Lappeenranta University of Technology, Department of Physics and Mathematics, Research Report (Jan. 1982).
Au, et al.; "Gene synthesis by a lcr-based approach: High-level production of leptin-I54 using synthetic gene in*Escherichia coli*,"; Biochemical and biophysical research communications, vol. 248, No. 1, pp. 200-203 (1998).
Bajic, et al.; "A simple suboptimal construction of cross-bifix-free codes"; Cryptography and Communications archive 6:27-37 (Aug. 8, 2013).
Bajic, et al.; "Distributed sequences and search process,"; Communications, IEEE International Conference on, vol. 1. IEEE, 2004, pp. 514-518 (2004).
Baldoni, et al.; "A user's guide for LattE integrale v1.7.2"; retrieved from https://www.math.ucdavis.edu/~latte/software/packages/latte_current/manual_v1.7.2.pdf on Mar. 8, 2017; (Oct. 2014).
Ban, et al., "Beyond trace reconstruction: Population recovery from the deletion channel," arXiv e-prints, p. arXiv:1904.05532, Apr. 2019.
Bancroft, C., et al.; "Long-term storage of information in DNA."; Science 293, 1763-1765 (2001).
Barg, et al.; "Codes in permutations and error correction for rank modulation,"; IEEE Trans. Inform. Theory; vol. 56, No. 7, pp. 3158-3165 (2010).
Barvinok; "A polynomial time algorithm for counting integral points in polyhedra when the dimension is fixed,"; Mathematics of Operations Research, vol. 19, No. 4, pp. 769-779 (1994).
Batu, et al., "Reconstructing strings from random traces," in Proceedings of the 15th Annual ACM-SIAM Symposium on Discrete Algorithms (SODA), 2004, pp. 910-918.
Beaucage, et al.; "Deoxynucleoside phosphoramiditesa new class of key intermediates for deoxypolynucleotide synthesis,"; Tetrahedron Letters, vol. 22, No. 20, pp. 1859-1862 (1981).

(56) References Cited

OTHER PUBLICATIONS

Benenson, et al.; "An autonomous molecular computer for logical control of gene expression,"; Nature, vol. 429, pp. 423-429 (May 2004).
Berman, P., et al.; "Approximating maximum independent set in bounded degree graphs."; In SODA, vol. 94, 365-371 (1994).
Bertalmio et al., "Image Inpainting", in Proceedings of the 27th annual conference on Computer graphics and interactive techniques. ACM Press/Addison-Wesley Publishing Co., 2000, pp. 417-424.
Bilotta, et al.; "A new approach to cross-bifix-free sets,"; IEEE Transactions on Information Theory, vol. 6, No. 58, pp. 4058-4063 (2012).
Binkowski, et al.; "Correcting errors in synthetic DNA through consensus shuffling,"; Nucleic acids research, vol. 33, No. 6, pp. e55-e55 (2005).
Blackburn, S. R.; "Non-overlapping codes."; arXiv preprint arXiv:1303.1026 (2013).
Blaum, M., et al.; "Error-correcting codes with bounded running digital sum."; IEEE transactions on information theory 39, 216-227 (1993).
Boneh, et al.; "Breaking DES using a molecular computer,"; Technical Report CS-TR-489-95, Department of Computer Science, Princeton University (1995).
Bornholt, et al.; "A dna-based archival storage system,"; Proceedings of the Twenty-First International Conference on Architectural Support for Programming Languages and Operating Systems; ACM, pp. 637-649 (2016).
Borovkov, et al.; "High quality gene assembly directly from unpurified mixtures of microarray synthesized oligonucleotides,"; Nucleic acids research, vol. 38, No. 19, pp. e180-e180 (2010).
Braich, et al.; "Solution of a 20-variable 3-SAT problem on a DNA computer,"; Science, vol. 296, pp. 492-502 (Apr. 2002).
Brakensiek, et al.; "Efficient low-redundancy codes for correcting multiple deletions,"; arXiv preprint arXiv:1507.06175 (2015).
Breslauer, et al.; "Predicting DNA duplex stability from the base sequence,"; Proc. Natl. Acad. Sci. USA, vol. 83, pp. 3746-3750 (1986).
Brill, et al.; "An improved error model for noisy channel spelling correction,"; Proceedings of the 38th Annual Meeting on Association for Computational Linguistics. Association for Computational Linguistics, pp. 286-293 (2000).
Bryksin, A. V., et al.; "Overlap extension PCR cloning: a simple and reliable way to create recombinant plasmids."; Biotechniques 48, 463 (2010).
Carr, et al.; "Protein-mediated error correction for de novo DNA synthesis,"; Nucleic acids research, vol. 32, No. 20, pp. e162-e162 (2004).
Chase, "New lower bounds for trace reconstruction," arXiv e-prints, p. arXiv:1905.03031, May 2019.
Chee, Y. M., et al.; "Cross-bifix-free codes within a constant factor of optimality."; Information Theory, IEEE Transactions on 59, 4668-4674 (2013).
Cheng, et al, "Deterministic document exchange protocols, and almost optimal binary codes for edit errors," in 2018 IEEE 59th Annual Symposium on Foundations of Computer Science (FOCS), Oct. 2018, pp. 200-211.
Church, G. M., et al.; "Next-generation digital information storage in DNA."; Science 337, 1628-1628 (2012).
Clote, et al.; "Computational Molecular Biology—An Introduction,"; Wiley Series in Mathematical and Computational Biology, New York (2000).
Cohen, G. D., et al.; "Dc-constrained error-correcting codes with small running digital sum."; Information Theory, IEEE Transactions on 37, 949-955 (1991).
Compeau, et al.; "How to apply de Bruijn graphs to genome assembly,"; Nature biotechnology, vol. 29, No. 11, pp. 987-991 (2011).
Cooke, et al.; "Polynomial construction of complex Hadamard matrices with cyclic core,"; Applied Mathematics Letters, vol. 12, pp. 87-93 (1999).
Cooper, et al.; "Generalized de Bruijn cycles,"; Annals of Combinatorics, vol. 8, No. 1, pp. 13-25 (2004).
Cullina, et al.; "An improvement to levenshtein's upper bound on the cardinality of deletion correcting codes,"; IEEE Transactions on Information Theory, vol. 60, No. 7, pp. 3862-3870 (2014).
Damerau; "A technique for computer detection and correction of spelling errors," Commun. ACM, vol. 7, No. 3, pp. 171-176 Available: http://doi.acm.org/10.1145/363958.363994 (Mar. 1964).
Davies, et al., "Reconstructing trees from traces," arXiv e-prints, p. arXiv:1902.05101, Feb. 2019.
Davis, J.; "Microvenus"; Art Journal 55, 70-74 (1996).
Notice of Allowance, U.S. Appl. No. 17/102,143, mailed May 4, 2023.
De Bruijn; "A combinatorial problem,"; *Koninklijke Nederlandse Akademie v. Wetenschappen*, vol. 49, No. 49, pp. 758-764 (1946).
De Lind Van Wijngaarden, et al.; "Frame synchronization using distributed sequences,"; Communications, IEEE Transactions on, vol. 48, No. 12, pp. 2127-2138 (2000).
De, at al., "Optimal mean-based algorithms for trace reconstruction," in Proceedings of the 49th Annual ACM SIGACT Symposium on Theory of Computing (STOC), 2017, pp. 1047-1056.
Delsarte; "An algebraic approach to the association schemes of coding theory,"; Doctoral dissertation, Universite Catholique de Louvain (1973).
Dormitzer, et al.; "Synthetic generation of influenza vaccine viruses for rapid response to pandemics,"; Science translational medicine, vol. 5, No. 185, pp. 185ra68-185ra68 (2013).
Erlich and Zielinski, "DNA Fountain enables a robust and efficient storage architecture", Science 355, 950-954 (Mar. 3, 2017).
Farnoud, et al.; "Error-correction in flash memories via codes in the Ulam metric,"; IEEE Trans. Inform. Theory; vol. 59, No. 5, pp. 3003-3020 (2013).
Farnoud, et al.; "Multipermutation codes in the Ulam metric for nonvolatile memories,"; Selected Areas in Communications IEEE Journal on; vol. 32, No. 5, pp. 919-932 (2014).
Fazeli, et al.; "Generalized Sphere Packing Bound,"; available at http://arxiv.org/abs/1401.6496 (2014).
Feng, J., et al.; "Identification of Single Nucleotides in MoS2 Nanopores,"; arXiv preprint, arXiv:1505.01608 (2015).
Feynman; "There's Plenty of Room at the Bottom,"; Caltech, Pasadena; Lecture (Dec. 29, 1959).
Fodor, et al.; "Light-directed, spatially addressable parallel chemical synthesis,"; Science, vol. 251 (1991).
Froehler, et al. "Synthesis of DNA via deoxynudeoside h-phosphonate intermediates,"; Nucleic Acids Research, vol. 14, No. 13, pp. 5399-5407 (1986).
Fuhrmann, et al.; "Removal of mismatched bases from synthetic genes by enzymatic mismatch cleavage,"; Nucleic acids research, vol. 33, No. 6, pp. e58-e58 (2005).
Gaborit, et al.; "Linear constructions for DNA codes,"; Theoretical Computer Science, vol. 334, No. 1-3, pp. 99-113 (Apr. 2005).
Gabrys et al., "The hybrid k-deck problem: Reconstructing sequences from short and long traces," in 2017 IEEE International Symposium on Information Theory (ISIT), Jun. 2017, pp. 1306-1310.
Gabrys, et al., "Sequence reconstruction over the deletion channel," IEEE Transactions on Information Theory, vol. 64, No. 4, pp. 2924-2931, Apr. 2018.
Gabrys, et al., "Unique reconstruction of coded sequences from multiset substring spectra," in 2018 IEEE International Symposium on Information Theory (ISIT), Jun. 2018, pp. 2540-2544.
Gabrys, et al.; "Asymmetric lee distance codes for DNA-based storage,"; arXiv preprint arXiv:1506.00740, published to arxiv.org on Jun. 2, 2015.
Gabrys, et al.; "Codes in the Damerau Distance for Deletion and Adjacent Transposition Correction"; arXiv:1601.06885, published to arxiv.org on Sep. 6, 2016.
Gabrys, et al.; "Graded bit-error-correcting codes with applications to flash memory,"; IEEE Transactions on Information Theory, vol. 59, No. 4, pp. 2315-2327 (2013).

(56) References Cited

OTHER PUBLICATIONS

Gallager; "Low-density parity-check codes,Information Theory"; IRE Transactions on, vol. 8, No. 1, pp. 2128, (1962).
Gao, et al.; "In situ synthesis of oligonucleotide microarrays,"; Biopolymers, vol. 73, No. 5, pp. 579-596 (2004).
Garegg, et al.; "Nucleoside h-phosphonates. iii. chemical synthesis of oligodeoxyribonucleotides by the hydrogenphosphonate approach,"; Tetrahedron letters, vol. 27, No. 34, pp. 4051-4054 (1986).
Ghindilis, et al.; "Combimatrix oligonucleotide arrays: genotyping and gene expression assays employing electrochemical detection,"; Biosensors and Bioelectronics, vol. 22, No. 9, pp. 1853-1860 (2007).
Gibson, et al.; "Chemical synthesis of the mouse mitochondrial genome,"; nature methods, vol. 7, No. 11, pp. 901-903 (2010).
Gibson; "Synthesis of dna fragments in yeast by one-step assembly of overlapping oligonucleotides,"; Nucleic acids research, p. gkp687 (2009).
Gilbert, E.; "Synchronization of binary messages."; Information Theory, IRE Transactions on 6, 470-477 (1960).
Gilbert; "A comparison of signalling alphabets,"; Bell System Technical Journal, vol. 31, No. 3, pp. 504-522 (1952).
Gilham, et al.; "Studies on polynucleotides. i. a new and general method for the chemical synthesis of the c5 internucleotidic linkage. syntheses of deoxyribo-dinucleotides1,"; Journal of the American Chemical Society, vol. 80, No. 23, pp. 6212-6222 (1958).
Gnerre, et al.; "High-quality draft assemblies of mammalian genomes from massively parallel sequence data,"; Proc. Natl. Acad. Sci. U.S.A., vol. 108, No. 4, pp. 1513-1518 (Jan. 2011).
Goldman, et al., "Towards practical, high-capacity, low-maintenance information storage in synthesized DNA," Nature, vol. 494, No. 7435, p. 77, 2013.
Goldman, N., et al.; "Towards practical, high-capacity, low-maintenance information storage in synthesized DNA."; Nature 494, 77-80 (2013).
Graham, et al.; "Lower bounds for constant weight codes,"; Information Theory, IEEE Transactions on, vol. 26, No. 1, pp. 37-43 (1980).
Grass, R. N., et al.; "Robust chemical preservation of digital information on DNA in silica with error-correcting codes."; Angewandte Chemie International Edition 54, 2552-2555 (Feb. 4, 2015).
Guibas, L. J., et al.; "Maximal prefix-synchronized codes."; SIAM Journal on Applied Mathematics 35, 401-418 (1978).
Guruswami, et al., Essential Coding Theory, 2018, draft available at https://cse.buffalo.edu/faculty/atri/courses/coding-theory/book.
Haeupler et al., "Repeated deletion channels," in 2014 IEEE Information Theory Workshop (ITW), Nov. 2014, pp. 152-156.
Haeupler, "Optimal document exchange and new codes for insertions and deletions," arXiv e-prints, p. arXiv:1804.03604, Apr. 2018.
Hagiwara; "A short proof for the multi-deletion error correction property of Helberg codes,"; IEICE Communications Express, vol. 5, No. 2, pp. 49-51 (Jan. 25, 2016).
Hall, et al.; "644. nucleotides. part xli. mixed anhydrides as intermediates in the synthesis of dinucleoside phosphates,"; Journal of the Chemical Society (Resumed), pp. 3291-3296 (1957).
Hall; "Notes on Coding Theory (Chapter 5—Generalized Reed-Solomon Codes)"; Department of Mathematics, Michigan State University; available online at http://users.math.msu.edu/users/jhall/classes/codenotes/coding-notes.html; (Jan. 7, 2015 revision).
Hall; "Notes on Coding Theory (Chapter 6—Modifying Codes)"; Department of Mathematics, Michigan State University; available online at http://users.math.msu.edu/users/jhall/classes/codenotes/coding-notes.html; (Jan. 7, 2015 revision).
Hall; "Notes on Coding Theory (Chapter 7—Codes over Subfields)"; Department of Mathematics, Michigan State University; available online at http://users.math.msu.edu/users/jhall/classes/codenotes/coding-notes.html; (Jan. 7, 2015 revision).
Hall; "Notes on Coding Theory (Chapter 8—Cyclic Codes)"; Department of Mathematics, Michigan State University; available online at http://users.math.msu.edu/users/jhall/classes/codenotes/coding-notes.html; (Jan. 7, 2015 revision).
Hall; "Notes on Coding Theory (Chapter 9—Weight and Distance Enumeration)"; Department of Mathematics, Michigan State University; available online at http://users.math.msu.edu/users/jhall/classes/codenotes/coding-notes.html; (Jan. 7, 2015 revision).
Heckel, et al., "Fundamental limits of DNA storage systems," in 2017 IEEE International Symposium on Information Theory (ISIT), Jun. 2017, pp. 3130-3134.
Heinrich; "Path decompositions,"; Le Matematiche, vol. 47, No. 2, pp. 241-258 (1993).
Helberg, et al.; "On multiple insertion/deletion correcting codes," Information Theory, IEEE Transactions on, vol. 48, No. 1, pp. 305-308 (2002).
Higuchi, et al.; "A general method of in vitro preparation and specific mutagenesis of dna fragments: study of protein and DNA interactions,"; Nucleic acids research, vol. 16, No. 15, pp. 7351-7367 (1988).
Hof, et al., "Capacity-achieving polar codes for arbitrarily permuted parallel channels,"; IEEE Trans. on Info. Theory; vol. 59, No. 3, pp. 1505-1516 (Mar. 2013).
Holden et al, "Lower bounds for trace reconstruction," arXiv e-prints, p. arXiv:1808.02336, Aug. 2018.
Holden, et al., "Subpolynomial trace reconstruction for random strings and arbitrary deletion probability," arXiv e-prints, p. arXiv:1801.04783, Jan. 2018.
Holenstein, et al., "Trace reconstruction with constant deletion probability and related results," in Proceedings of the 19th Annual ACM-SIAM Symposium on Discrete Algorithms (SODA), 2008, pp. 389-398.
Horovitz, et al., "Reconstruction of sequences over non-identical channels," IEEE Trans-actions on Information Theory, vol. 65, No. 2, pp. 1267-1286, Feb. 2019.
Huffman, "A Method for the Construction of Minimum-Redundancy Codes", Proceedings of the I.R.E., Sep. 1952, pp. 1098-1101.
Hughes, et al.; "Expression profiling using microarrays fabricated by an ink-jet oligonucleotide synthesizer,"; Nature biotechnology, vol. 19, No. 4, pp. 342-347 (2001).
Jacquet, et al.; "Counting Markov types, balanced matrices, and Eulerian graphs,"; IEEE Trans. Inform. Theory; vol. 58, No. 7, pp. 4261-4272 (2012).
Jansen, et al.; "Identification of genes that are associated with dna repeats in prokaryotes,"; Molecular microbiology, vol. 43, No. 6, pp. 1565-1575 (2002).
Jiang, et al.; "Rank modulation for flash memories,"; IEEE Trans. Inform. Theory; vol. 55, No. 6, pp. 2659-2673 (2009).
Johnson; "A new upper bound for error-correcting codes,"; Information Theory, IRE Transactions on, vol. 8, No. 3, pp. 203-207 (1962).
Kannan, et al.; "More on reconstructing strings from random traces: insertions and deletions,"; Proc. IEEE Intl. Inform. Theory; IEEE; pp. 297-301. (2005).
Kaykobad, "Positive solutions of positive linear systems,"; Lin. Alg. and its App., vol. 64, pp. 133-140 (Jan. 1985).
Khorana, et al.; "Syntheses of dideoxyribonucleotides,"; Journal of the American Chemical Society, vol. 79, No. 4, pp. 1002-1003 (1957).
Kiah, et al.; "Codes for DNA sequence profiles,"; arXiv preprint; arXiv:1502.00517, published to arxiv.org on Feb. 2, 2015.
Kiah, et al.; "Codes for DNA storage channels,"; arXiv preprint arXiv:1410.8837, published to arxiv.org on Oct. 31, 2014.
Kim, et al.; "Shotgun DNA synthesis' for the high-throughput construction of large DNA molecules,"; Nucleic acids research, p. gks546 (2012).
King; "Bounds for DNA codes with constant GC-content,"; The Electronic Journal of Combinatorics, vol. 10, No. 1, #R33 (2003).
Kløve; "Error correcting codes for the asymmetric channel."; Department of Pure Mathematics, University of Bergen, (1981).
Knuth; "Efficient balanced codes,"; Information Theory, IEEE Transactions on, vol. 32, No. 1, pp. 51-53 (1986).
Kong, et al.; "Parallel gene synthesis in a microfluidic device,"; Nucleic acids research, vol. 35, No. 8, p. e61, (2007).

(56) References Cited

OTHER PUBLICATIONS

Kosuri, et al.; "Large-scale de novo dna synthesis: technologies and applications,"; Nature methods, vol. 11, No. 5, pp. 499-507 (2014).
Kosuri, et al.; "Scalable gene synthesis by selective amplification of dna pools from high-fidelity microchips,"; Nature biotechnology, vol. 28, No. 12, pp. 1295-1299 (2010).
Kovacevic et al., "Codes in the space of multisets—Coding for permutation channels with impairments," IEEE Transactions on Information Theory, vol. 64, No. 7, pp. 5156-5169, Jul. 2018.
Krishnamurthy, et al., "Trace reconstruction: Generalized and parameterized," arXiv e-prints, p. arXiv:1904.09618, Apr. 2019.
Kulkarni, et al.; "Nonasymptotic upper bounds for deletion correcting codes,"; IEEE Trans. on Info. Theory, vol. 59, No. 8, pp. 5115-5130 (Apr. 2013).
Kumar and Milenkovic, "On Unequal Error Protection LDPC Codes Based on Plotkin-Type Constructions", IEEE Transactions on Communication, vol. 54, No. 6, Jun. 2006, pp. 994-1005.
Kumar, et al.; "Mega3: integrated software for molecular evolutionary genetics analysis and sequence alignment,"; Briefings in bioinformatics, vol. 5, No. 2, pp. 150-163 (2004).
Lander, et al.; "Initial sequencing and analysis of the human genome,"; Nature, vol. 409, No. 6822, pp. 860-921 (Feb. 2001).
Lee, et al.; "A high-throughput optomechanical retrieval method for sequence-verified clonal DNA from the ngs platform,"; Nature communications, vol. 6 (2015).
Lenz, et al., "Coding over sets for DNA storage," in 2018 IEEE International Symposium on Information Theory (ISIT), Jun. 2018, pp. 2411-2415.
LeProust, et al.; "Synthesis of high-quality libraries of long (150mer) oligonucleotides by a novel depurination controlled process,"; Nucleic acids research, vol. 38, No. 8, pp. 2522-2540 (2010).
Letsinger, et al.; "Oligonucleotide synthesis on a polymer support1, 2," Journal of the American Chemical Society, vol. 87, No. 15, pp. 3526-3527 (1965).
Letsinger, et al.; "Synthesis of thymidine oligonucleotides by phosphite triester intermediates,"; Journal of the American Chemical Society, vol. 98, No. 12, pp. 3655-3661 (1976).
Letsinger, et al; "Synthesis of oligothymidylates via phosphotriester intermediates,"; Journal of the American Chemical Society, vol. 91, No. 12, pp. 3350-3355 (1968).
Levenshtein, "Efficient reconstruction of sequences," IEEE Transactions on Information Theory, vol. 47, No. 1, pp. 2-22, Jan. 2001.
Levenshtein; "Binary codes capable of correcting deletions, insertions, and reversals," in Soviet physics doklady, vol. 10, No. 8, pp. 707-710 (1966).
Li, et al.; "De novo assembly of human genomes with massively parallel short read sequencing," Genome Res., vol. 20, No. 2, pp. 265-272 (Feb. 2010).
Ma, et al.; "DNA synthesis, assembly and applications in synthetic biology,"; Current opinion in chemical biology, vol. 16, No. 3, pp. 260-267 (2012).
Ma, et al.; "Error correction in gene synthesis technology,"; Trends in biotechnology, vol. 30, No. 3, pp. 147-154 (2012).
Magner, et al, "Fundamental bounds for sequence reconstruction from nanopore sequencers," IEEE Transactions on Molecular, Biological and Multi-Scale Communications, vol. 2, No. 1, pp. 92-106, Jun. 2016.
Mansuripur, et al.; "Information storage and retrieval using macromolecules as storage media,"; University of Arizona Technical Report (2003).
Marathe, et al.; "On combinatorial DNA word design,"; J. Comput. Biol., vol. 8, pp. 201-219 (2001).
Massey, J. L.; "Optimum frame synchronization."; Communications, IEEE Transactions on 20, 115-119 (1972).
Matzas, et al.; "Highfidelity gene synthesis by retrieval of sequence-verified dna identified using high-throughput pyrosequencing,"; Nature biotechnology, vol. 28, No. 12, pp. 1291-1294 (2010).
Mazumdar, et al.; "Coding for high-density recording on a 1-D granular magnetic medium,"; IEEE Trans. on Info. Theory, vol. 57, No. 11, pp. 7403-7417 (Jun. 2011).
McGregor, et al., "Trace reconstruction revisited," in Algorithms—ESA 2014, A. S. Schulz and D. Wagner, Eds. Berlin, Heidelberg: Springer Berlin Heidelberg, 2014, pp. 689-700.
Medvedev, et al.; "Computability of models for sequence assembly,"; Algorithms in Bioinformatics; Springer; pp. 289-301 (2007).
Meunier et al, Recombination Drives the Evolution of GC-Content in the Human Genome Molecular Biology and Evolution, vol. 21, pp. 984-990 (2004).
Michelson, et al.; "Nucleotides part xxxii. synthesis of a dithymidine dinucleotide containing a 3': 5'-internucleotidic linkage,"; Journal of the Chemical Society (Resumed), pp. 2632-2638 (1955).
Wetterstrand. "Nanopore DNA Sequencing", National Human Genome Institute, updated Feb. 2, 2024, accessed Feb. 2, 2024 [https://www.genome.gov/genetics-glossary/Nanopore-DNA-Sequencing#:~:text=Nanopore%20DNA%20sequencing%20is%20a,use%20to%20develop%20and%20operate].
Holenstein et al., "Trace reconstruction with constant deletion probability and related results," Research Gate, Conference Paper, Jan. 2008, 13 pages.
Office Action, U.S. Appl. No. 16/653,564, mailed Jul. 20, 2023.
Office Action, U.S. Appl. No. 16/653,564, mailed Feb. 29, 2024.

* cited by examiner

CODED TRACE RECONSTRUCTION

CROSS-REFERENCE TO RELATED APPLICATION

The present application claims the benefit of U.S. Patent Application No. 62/925,332, filed Oct. 24, 2019, the content of which is herewith incorporated by reference.

STATEMENT ON FEDERALLY SPONSORED RESEARCH OR DEVELOPMENT

This invention was made with Government support under Grant No. CCF 16-18366 (National Science Foundation) and W911NF-18-2-0032 OM (DARPA Molecular Informatics). The Government has certain rights in the invention.

BACKGROUND

Trace reconstruction was originally motivated by problems in sequence alignment, phylogeny, and computational biology. The goal of trace reconstruction is to reconstruct an unknown binary string x given random portions or "traces" of x where each trace is generated by deleting each coordinate of x independently with probability p<1. Put another way, the setting for the problem is as follows: There is an unknown string $x \in \{0, 1\}^n$, and the goal is to reconstruct the string. Towards this goal, traces of x are made available, which are obtained by sending x through a deletion channel. This deletion channel independently deletes bits of x with a given deletion probability d. Accordingly, each trace corresponds to a subsequence of x.

In this scenario, the traditional optimization problem is to minimize the number of traces required for reconstructing x with high probability. Since its introduction, the problem of trace reconstruction has been studied from several different perspectives.

Two of the main perspectives correspond to "worst-case trace reconstruction", where the reconstruction algorithm must work simultaneously for all strings in $\{0, 1\}^n$, and "average-case trace reconstruction," where the reconstruction algorithm is only required to work with high probability, taken over the choice of string and the randomness of the reconstruction algorithm for a uniformly random string. The number of traces required for average-case trace reconstruction is, as expected, much smaller than that required for worst-case trace reconstruction. The problem in question has also been studied from a combinatorial coding perspective.

Previous work on average-case trace reconstruction can be interpreted from a coding theoretic perspective: They state that there exist very large codebooks which can be reconstructed efficiently from relatively few traces. However, no efficient encoders are known for such codes, and it may be possible to further reduce the number of traces required for reconstruction by relaxing the size of the code.

This point of view naturally leads to the problem of coded trace reconstruction: The goal is to design high rate, efficiently encodable codes whose codewords can be efficiently reconstructed with high probability from very few traces with constant deletion probability. Here, "high rate" refers to a rate approaching 1 as the block length increases. In such a case, the number of traces must grow with the block length of the code. Coded trace reconstruction is also closely related to and motivated by the read process in portable DNA-based data storage systems.

A practical motivation for coded trace reconstruction comes from portable DNA-based data storage systems using DNA nanopores. In DNA-based storage, a block of user-defined data is first encoded over the nucleotide alphabet {A, C, G, T}, and then transformed into moderately long strands of DNA through a DNA synthesis process. For ease of synthesis, the DNA strands are usually encoded to have balanced GC-content, so that the fraction of {A, T} and {G, C} bases is roughly the same. To recover the block of data, the associated strand of DNA is sequenced with nanopores, resulting in multiple corrupted reads of its encoding. Although the errors encountered during nanopore sequencing include both deletions/insertions as well as substitution errors, careful read preprocessing alignment allows the processed reads to be viewed as traces of the data block's encoding. As a result, recovering the data block in question can be cast in the setting of trace reconstruction. Due to practical time constraints (e.g., sequencing time), it is of great interest to minimize the number of reads required to reconstruct the data block.

The trace reconstruction procedures associated to the codes used by practical portable DNA-based storage systems are largely based on heuristics. Conventional trace reconstruction algorithms operate on carefully designed coded strings, but make use of multiple sequence alignment algorithms which are difficult to analyze rigorously. For example, an example conventional trace reconstruction algorithm does not make use of specific read-error correction codes and is a variation of the Bitwise Majority Alignment (BMA) algorithm. However, the BMA algorithm is only known to be robust when the errors correspond to independent and identically distributed (i.i.d.) deletions and the fraction of errors is at most $O(1/\log n)$, where n denotes the blocklength of the code. Moreover, the conventional codes have been designed only for a fixed blocklength. As a result, such codes have poor robustness or performance guarantees for trace reconstruction even under i.i.d. deletions with constant deletion probability.

Accordingly, there exists a need for a coded trace reconstruction method that offers improved robustness and performance for trace reconstruction in portable DNA-based data storage systems.

SUMMARY

The present disclosure describes methods that can provide coded trace reconstruction for efficient, high-rate codes against a constant rate of deletions, among other possibilities. Namely, the disclosure describes the design and analysis of high-rate efficiently encodable codes that can be efficiently decoded with high probability from few traces (also called reads) that are corrupted by edit errors.

In a first aspect, method is provided. The method includes receiving a message having a message length n bits. The method also includes partitioning the message into a plurality of blocks with a maximum block length of $O(\log^2 n)$. The method additionally includes encoding each block to provide a plurality of encoded blocks and inserting unique markers between the encoded blocks so as to form an encoded message. The markers each have a minimum marker length $O(\log n)$. The method also includes causing a DNA sequencer to synthesize a nucleotide sequence based on the encoded message.

In a second aspect, a method is provided. The method includes receiving, at a DNA readout system, a nucleotide sequence. The method additionally includes reading the nucleotide sequence based on an alphabet consisting of {adenine (A), cytosine (C), guanine (G), and thymine (T)}. The method further includes determining positions of unique markers between a plurality of encoded blocks in the nucleotide sequence and decoding each encoded block of the plurality of encoded blocks according to an inner code, forming a plurality of decoded blocks. The method yet further includes appending the decoded blocks to one another to provide a decoded message with message length n bits.

In a third aspect, A DNA-based sequencing system is provided. The DNA-based sequencing system includes a DNA sequencer and a controller configured to carry out operations. The operations include receiving a message having a message length n bits. The operations additionally include partitioning the message into a plurality of blocks with a maximum block length of $O(\log^2 n)$. The operations also include encoding each block to provide a plurality of encoded blocks and inserting unique markers between the encoded blocks so as to form an encoded message. The markers each have a minimum marker length $O(\log n)$. The operations additionally include causing the DNA sequencer to synthesize a nucleotide sequence based on the encoded message.

In a fourth aspect, a DNA-based readout system is provided. The DNA-based readout system includes a DNA reader and a controller configured to carry out operations. The operations include receiving, at a DNA reader, a nucleotide sequence and reading the nucleotide sequence based on an alphabet consisting of {adenine (A), cytosine (C), guanine (G), and thymine (T)}. The operations additionally include determining positions of unique markers between a plurality of encoded blocks in the nucleotide sequence and decoding each encoded block of the plurality of encoded blocks according to an inner code, so as to form a plurality of decoded blocks. The operations yet further include appending the decoded blocks to one another to provide a decoded message with message length n bits.

Other aspects, embodiments, and implementations will become apparent to those of ordinary skill in the art by reading the following detailed description, with reference where appropriate to the accompanying drawings.

DETAILED DESCRIPTION

Figure 1:
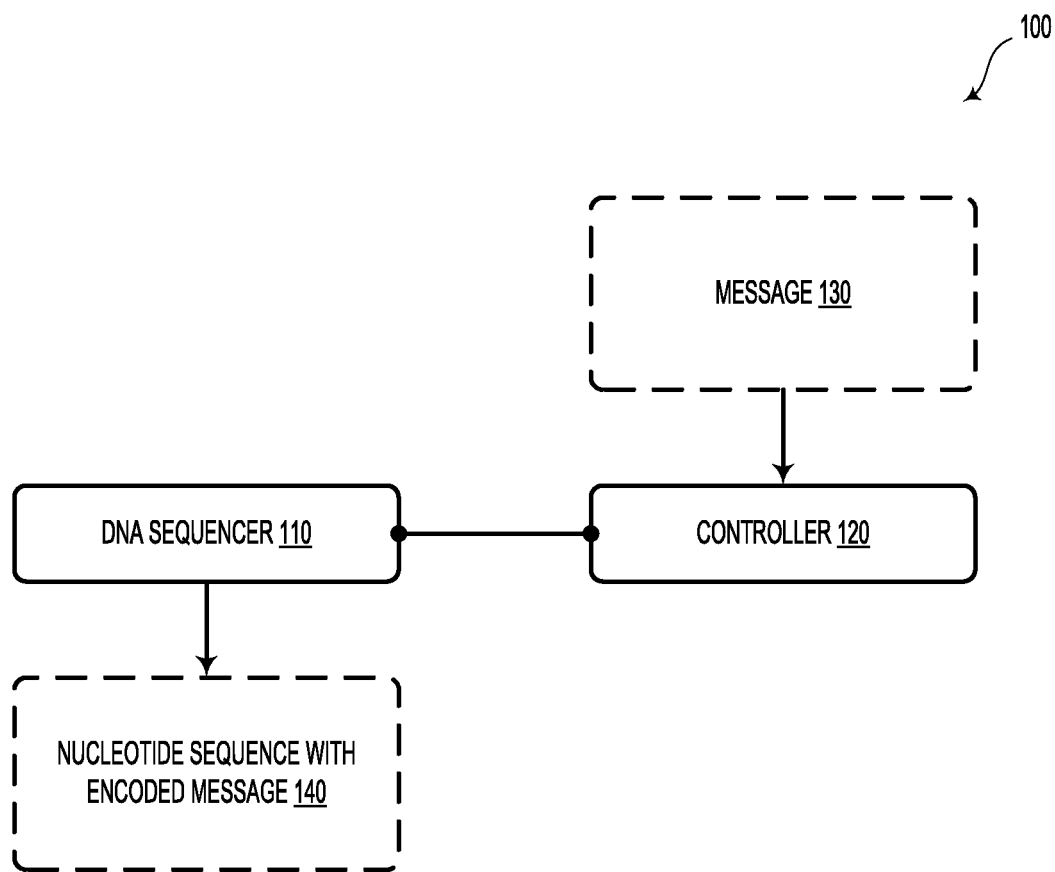
FIG. 1 illustrates a DNA-based sequencing system, according to an example embodiment.

Example methods, devices, and systems are described herein. It should be understood that the words "example" and "exemplary" are used herein to mean "serving as an example, instance, or illustration." Any embodiment or feature described herein as being an "example" or "exemplary" is not necessarily to be construed as preferred or advantageous over other embodiments or features. Other embodiments can be utilized, and other changes can be made, without departing from the scope of the subject matter presented herein.

Thus, the example embodiments described herein are not meant to be limiting. Aspects of the present disclosure, as generally described herein, and illustrated in the figures, can be arranged, substituted, combined, separated, and designed in a wide variety of different configurations, all of which are contemplated herein.

Further, unless context suggests otherwise, the features illustrated in each of the figures may be used in combination with one another. Thus, the figures should be generally viewed as component aspects of one or more overall embodiments, with the understanding that not all illustrated features are necessary for each embodiment.

As described herein, a channel model may be utilized to represent a nanopore system as follows. For a given input string $x \in \{0, 1\}n$, a deletion probability d, and an integer $t(n)$, the channel returns $t(n)$ traces of x. Each trace of x is obtained by sending x through a deletion channel with deletion probability d. In such a scenario, the deletion channel deletes each bit of x independently with probability d, and outputs a subsequence of x containing all bits of x that were not deleted in order. The $t(n)$ traces are independent and identically distributed (i.i.d.) as outputs of the deletion channel for input x.

Given a code $C \subseteq \{0, 1\}n$, C can be efficiently reconstructed from $t(n)$ traces if there exists a polynomial $p(n)$ and a polynomial-time algorithm that recovers every $c \in C$ from $t(n)$ traces of c with probability at least $1-1/p(n)$ over the probability distribution of the traces.

1. Overview

Coded trace reconstruction is described herein within the context of determining efficient, high-rate codes against a constant rate of trace deletions. More specifically, the performance of marker-based constructions is analyzed with worst-case trace reconstruction algorithms. These constructions have the advantage that they can be easily adapted to work with a large range of inner codes.

At a high level, the construction operates by splitting an n-bit message into short blocks of length $O(\log^2 n)$, encoding each block with an inner code satisfying a certain constraint, and adding markers of length $O(\log n)$ between the blocks. The structure of the markers and the property of the inner code imply that, with high probability, we can split the traces into many shorter sub-traces associated with substrings of length $O(\log^2 n)$, and then apply the worst-case trace reconstruction algorithm on the sub-traces. The main result in this context is Theorem 1.

Theorem 1. For every constant deletion probability $d<1$, there exists an efficiently encodable code $C \subseteq \{0, 1\}^{n+r}$ with redundancy $r=O(n/\log n)$ that can be efficiently reconstructed from $\exp(O(\log^{2/3} n))$ traces.

The above construction is relevant as it shows that marker-based construction can be utilized with any inner code satisfying a simple constraint and iterate the marker-based construction by further dividing each block of length $\log^2 n$ into blocks of length $(\log \log n)^2$ and adding markers of length $O(\log \log n)$ between them. In this setting, it is almost guaranteed that reconstruction of a small fraction of blocks will fail. Nevertheless, this problem can be easily resolved by adding error-correction redundancy to the string to be encoded.

This leads to the following result, which can be extended beyond two marker levels.

Theorem 2. For every constant deletion probability $d<1$, there exists an efficiently encodable code $C \subseteq \{0, 1\}^{n+r}$ with redundancy $r=O(n/\log \log n)$ that can be efficiently reconstructed from $\exp(O(\log \log n)^{2/3})$ traces.

In some embodiments, the marker-based constructions can be implemented with a large range of inner codes to construct high-rate marker-based codes over the {A, C, G, T} alphabet with two important properties: The codes have balanced GC-content and provably require few traces to be efficiently reconstructed. Such embodiments may be similar to the marker-based constructions above, but with different markers and an inner code over a larger alphabet and with stronger constraints. In this context, the following results can be obtained.

Theorem 3. For every constant deletion probability d<1, there exists an efficiently encodable code $C \subseteq \{A, C, G, T\}^{n+r}$ with redundancy r=O(n/log n) and balanced GC-content that can be efficiently reconstructed from $\exp(O(\log^{2/3} n))$ traces.

Theorem 4. For every constant deletion probability d<1, there exists an efficiently encodable code $C \subseteq \{A, C, G, T\}^{n+r}$ with redundancy r=O(n/log log n) and balanced GC-content that can be efficiently reconstructed from $\exp(O(\log \log n)^{2/3})$ traces.

The result of Theorem 1 may be further improved by considering a more careful design of the highrate inner code to be used in the marker-based constructions, provided that the deletion probability is a small enough constant. This allows for using a modified version of an algorithm for average-case trace reconstruction, which leads to a substantial reduction in the number of traces required for reconstruction and barely any rate changes. As a first step towards achieving this goal, a low-redundancy code is described that can be efficiently reconstructed from polynomially many traces. The proposed coding scheme relies on the fact that n-bit messages into strings that are almost subsequence-unique via explicit constructions of almost k-wise independent spaces can be efficiently encoded.

The average-case trace reconstruction algorithm operates on subsequence-unique strings, and an adaptation of the algorithm can provide the following result.

Theorem 5. If the deletion probability is a small enough constant, there exists an efficiently encodable code $C \subseteq \{0, 1\}^{n+r}$ with redundancy r=O(log n) that can be efficiently reconstructed from poly(n) traces.

An important step is to adapt this code for use as an inner code in the marker-based construction. Some care is needed, since the global structure of the strings changes significantly due to the presence of the markers. In particular, the bootstrapping method in the trace reconstruction algorithm no longer works. In such scenarios, the following result can be found.

Theorem 6. If the deletion probability is a small enough constant, there exists an efficiently encodable code $C \subseteq \{0, 1\}^{n+r}$ with redundancy r=O(n/log n) that can be efficiently reconstructed from poly(log n) traces.

For simplicity, the present description mostly focuses on constructions of binary codes, although it provides some guidelines and simple coding procedures for quaternary codes. It will be understood that coded trace reconstruction is inherently more difficult for smaller alphabets.

The present disclosure provides ways to reduce the read time-delay and increases the reliability of nanopore readouts for DNA-based data storage. This is achieved, at least in part, by carefully encoding information to allow for reconstruction in the presence of very few reads with high deletion probabilities.

2. Notation and Preliminaries
2.1 Notation

We denote the length of a string x by |x|, and its Hamming weight by $w(x) = |\{i : x_i \neq 0\}|$. Given two strings x and y over the same alphabet, we denote their concatenation by x||y. For a string x, we define $x[a, b) = (x_a, x_{a+1}, \ldots, x_{b-1})$ and $x[a, b] = (x_a, x_{a+1}, \ldots, x_b)$. If |x|=n, we define $x[a, \bullet] = (x_a, x_{a+1}, \ldots, x_n)$.

We say that y is a subsequence of x if there exist indices $i_1 < i_2 < \ldots < i_{|y|}$ such $x_{i_j} = y_j$. Moreover, y is said to be a substring of x if $y = x[a, a+|y|)$ for some $1 \leq a \leq |x| - |y| + 1$. Given two strings x, y∈{0, 1}n, we write x+y for the bitwise XOR of x and y. A run of length f in a string x is a substring of x comprising f identical symbols. Sets are denoted by bold letters such as S and T. Random variables are denoted by uppercase letters such as X, Y, and Z. The uniform distribution over $\{0, 1\}t$ is denoted by $U_t$, and the binomial distribution on n trials with success probability p is denoted by Bin(n, p). The binary entropy function is denoted by h and all logarithms log are taken with respect to the base 2.

2.2 Almost k-Wise Independent Spaces

We start by defining almost k-wise independence and present a related result that we will find useful in our future derivations.

Definition 7 (ε-almost k-wise independent random variable). A random variable $X \in \{0, 1\}m$ is said to be ε-almost k-wise independent if for all sets of k distinct indices $i_1, i_2, \ldots, i_k$ we have $|\Pr[X_{i_1} = x_1, \ldots, X_{i_k} = x_k] - 2^{-k}| \leq \epsilon$ for all $(x_1, \ldots, x_k) \in \{0, 1\}k$.

The following result gives an efficient construction of an ε-almost k-wise independent space which can be generated from few uniformly random bits.

Lemma 8. For every m, k, and ε, there exists an efficiently computable function g: $\{0, 1\}t \to \{0, 1\}m$ with $$t = O\left(\log\left(\frac{k \log m}{\epsilon}\right)\right)$$

such that $g(U_t)$ is an ε-almost k-wise independent random variable over $\{0, 1\}m$, where $U_t$ denotes the uniform distribution over $\{0, 1\}t$.

2.3 Nearly-Optimal Systematic Codes for Edit Errors

We require systematic codes that are robust against edit errors (deletions and insertions). Nearly-optimal systematic codes for adversarial edit errors have been recently constructed using optimal protocols for deterministic document exchange. The following result is relevant to our analysis.

Lemma 9. For every m and t<m there exists an efficiently encodable and decodable systematic code $C_{edit} \subseteq \{0, 1\}^{m+r}$ with encoder $Enc_{edit}: \{0, 1\}m \to \{0, 1\}^{m+r}$ and redundancy $$r = O\left(t \log^2 \frac{m}{t} + t\right)$$

that can efficiently correct up to t edit errors. In particular, if $t = \Theta(m)$, then the redundancy is r=O(m).

2.4 Trace Reconstruction

Next, we discuss several results pertaining to the worst-case and average-case trace reconstruction problem that will be useful for our constructions.

2.4.1 Worst-Case Trace Reconstruction

For worst-case reconstruction, a result used in Section 3 is summarized below.

Lemma 10. For every n and constant deletion probability d, there exists an algorithm that reconstructs an arbitrary string $x \in \{0, 1\}n$ with probability at least $1 - \exp(-2n)$ from $\exp(O(n^{1/3}))$ traces in time $\exp(O(n^{1/3}))$ 2.4.2 Trace Reconstruction of Subsequence-Unique Strings One of the key tools for our constructions in Section 4 is a modified version of the efficient trace reconstruction algorithm for what we refer to as subsequence-unique strings. This algorithm may also be used for average-case trace reconstruction. We start by defining subsequence-unique strings.

Definition 11 (w-sub sequence-unique string). A string $x \in \{0, 1\}n$ is said to be w-sub sequence-unique if for every a and b such that either a<b or b+1.1w<a+w we have that the substring x[a, a+w) is not a subsequence of x[b, b+1.1w).

Note that these strings have been under the name "sub string-unique" in other work. We proposed the name change to avoid confusion with a different definition under the same name, described herein. The following result about subsequence-unique strings was established previously.

Lemma 12. For w=100 log n and a small enough constant deletion probability d, there exists an algorithm that reconstructs every w-sub sequence-unique string $x \in \{0, 1\}n$ with probability 1−1/poly(n) from poly(n) traces in time poly(n).

Since a uniformly random string is w-subsequence-unique with high probability, Lemma 12 applies to average-case trace reconstruction. As we make explicit use of the algorithm behind Lemma 12, for the sake of clarity, we provide next a more in-depth discussion of the method. However, before we proceed to the actual description of the algorithm, we briefly introduce some definitions and basic related results.

Given integers i and j and a deletion probability d, we denote the probability that the i-th bit of a string appears as the j-th bit of its trace by PQ, j). Then, we have $$P(i, j) = \binom{i-1}{j-1}(1-d)^j d^{i-j}.$$

The following lemma states some useful properties of P(i, j).

Lemma 13. If $j \leq (1-3d)i$, then $P(i,j) \geq 2\Sigma_{i' > i} P(i',j)$. Furthermore, if $(1-4d)i < j < (1-3d)i$, we have $P(i,j) \geq \exp(-6di)$.

Intuitively, the second part of Lemma 13 means that we have a good idea of the position of x; in the trace if i is small. The following result makes use of this. It states that we can recover the first O(log n) bits of an arbitrary string with poly(n) traces, which is required to bootstrap the trace reconstruction algorithm.

Lemma 14. Fix a string $x \in \{0, 1\}^n$, and suppose that we know $x_1, \ldots, x_{h-1}$. Then, there is an algorithm that recovers $x_h$ from exp(O(hd log(1/d))) traces of x with probability 1−o(1), provided that d<⅓.

In the second part of the algorithm, we must look for matchings of certain strings within the traces. To this end, we introduce the following definition.

Definition 15. Fix a string $x \in \{0, 1\}n$, and let T denote its trace. Then, we say that there is a matching of x[a, b) in T if there exists some u such that T [u−(b−a), u)=x[a, b).

Matchings of w-subsequence-unique strings have useful properties, as formalized in the following lemma.

Lemma 16. If x is w-subsequence-unique and there is a matching of x[a, a+w) in T, say at T[u−w, u), then the probability that $T_{u-1}$ does not come from x[a+w, a+1.1w) is at most $nd^{0.001w}$.

We are now in a position to describe an algorithm introduced previously. We begin by setting w=100 log n, v=w/d, and j=(v−0.1w)(1−3d). Then, to recover a w-subsequence-unique string x, we proceed with two steps: First, we use the algorithm from Lemma 14 to recover the first v bits of x with poly(n) traces. Now, suppose we have recovered $x_1, \ldots, x_{i-1}$ for i−1≥v. Our next goal is to recover $x_i$ with poly(n) traces.

Note that if i is relatively large, we cannot use the algorithm from Lemma 14 to recover x; anymore, as it would require more than poly(n) traces. To achieve our goal, we instead focus on finding matchings of the substring x[i−v−w, i−v) within the trace. Let T denote a trace of x, and suppose there is a matching of x[i−v−w, i−v) in T at positions T [u−w, u). Then, we set V=T [u, •], i.e., we let V be the suffix of the trace following the matching. The key property is that $Pr[V_j=1]$ satisfies a threshold property depending on the value of $x_i$. More precisely, there exist two positive values $B_1 > B_0$ sufficiently far apart such that $Pr[V_j=1] \leq B_0$ if $x_i=0$ and $Pr[V_j=1] \geq B_1$ if $x_i=1$. Moreover, all terms in these inequalities can be estimated with a small error from poly(n) traces of x. As a result, we can reliably estimate x; by checking whether $Pr[V_j=1] \leq B_0$ or $Pr[V_j=1] \geq B_1$.

We prove next the threshold property for $Pr[V_j=1]$. Let R denote the position in x of the bit appearing in position u−1 in the trace T of the matching for x[i−v−w, i−v). In other words, R denotes the position in x of the last bit appearing in the matching in T. We may write $$Pr[V_j = 1] = \sum_{r=1}^{n} Pr[R = r] \, Pr[V_j = 1 \mid R = r]$$

$$= \epsilon_i(x) + \sum_{r=i-v}^{i-v+0.1w} Pr[R = r] \, Pr[V_j = 1 \mid R = r]$$

$$= \epsilon_s(x) + \sum_{r=i-v}^{i-v+0.1w} Pr[R = r] \sum_{\ell=a+1}^{n} P(\ell - r, j) x_\ell$$

$$= \epsilon_x(x) + \sum_{r=i-v}^{i-v+0.1w} Pr[R = r] \sum_{\ell=i+1}^{i-1} P(\ell - r, j) x_\ell$$

$$+ \sum_{r=i-v}^{i-v+0.1w} Pr[R = r] \left( P(i - r, j) x_i + \sum_{\ell=i+1}^{n} P(\ell - r, j) x_\ell \right),$$

where the second equality follows from Lemma 16 with $0 \leq \epsilon(x) \leq nd^{0.001w}$. Using the first part of Lemma 13, we conclude that $\sum_{\ell} P(\ell - r, j) \leq \frac{1}{2} P(i - r, j)$, As a result, we have $$x_i = 0 \Rightarrow Pr[V_j = 1] \leq \epsilon_i(x) + \sum_{r=i-v}^{i-v+0.1w} Pr[R = r] \sum_{\ell=r+1}^{i-1} P(\ell - r, j) x_\ell + \quad (1)$$

$$\frac{1}{2} \sum_{r=i-v}^{i-v+0.1w} Pr[R = r] P(i - r, j)$$

and $$x_i = 1 \Rightarrow Pr[V_j = 1] \geq \epsilon_i(x) + \sum_{r=i-v}^{i-v+0.1w} Pr[R = r] \sum_{\ell=r+1}^{i-1} P(\ell - r, j) x_\ell + \quad (2)$$

$$\sum_{r=i-v}^{i-v+0.1w} Pr[R = r] P(i - r, j).$$

By the second part of Lemma 13, since i−r≤v and v=w/d, we have $P(i-r,j) \geq 2^{-9w}$. Combining this with Lemma 16 ford small enough means that the gap between the right hand side of (1) and (2) is at least $2^{-(9w+1)}$. To finalize the argument, we note that (i) we can efficiently approximate $Pr[V_j=1]$ to within an error of, say, $2^{-100w}$ with high probability from poly(n) traces of x, and (ii) we can efficiently approximate $Pr[R=r|R<i]$ to within the same error given that we know $x_1, \ldots, x_{i-1}$, provided d is small enough. Since $Pr[R<i] \geq 1 - nd^{-0.001w}$ by Lemma 16, we can further efficiently approximate $Pr[R=r]$ to within an error of, say, $2^{-50w}$ with high probability. From these observations, it follows that we can estimate $x_i$ correctly with high probability from poly(n) traces, where the degree of the polynomial is independent of i, as desired.

3. Marker-Based Constructions

This section describes simple constructions of high-rate codes that can be efficiently reconstructed from a few traces. The idea behind the approach is the following: Each codeword contains markers, consisting of sufficiently long runs of 0's and 1's. Between two consecutive markers, we add a short block containing a codeword from an inner code satisfying a mild constraint.

Intuitively, the runs in the markers will still be long in the trace, and so we hope to be able to correctly identify the positions of all markers in a trace with high probability. After this is done, the trace can be split into many shorter, independent sub-traces corresponding to a block (and possibly some bits from the two markers delimiting it). Then, a worst-case trace reconstruction algorithm can be applied to the sub-traces. The savings in the number of traces required for reconstruction stem from the fact that subtraces are short, and that each trace can be utilized simultaneously (and independently) by all blocks. This idea for reconstruction almost works as is, except that the process of identifying the markers in a trace may be affected by long runs of 0's originating from a block between two markers. However, this can be easily solved by requiring that all runs of 0's in each block are short enough. Many codes, including codes with low redundancy, satisfy the desired property, and hence make for good candidates for the inner code.

We describe and analyze a code based on the idea discussed above in Section 3.1. Then, we consider a follow-up construction in Section 3.2 which requires fewer traces, at the expense of a decrease in the rate. At a high-level, this second code is obtained by introducing two levels of markers and adding some simple error-correction redundancy to the message prior to other encodings. Finally, in Section 3.3, we extend these ideas to the $\{A, C, G, T\}$ alphabet in order to obtain high-rate codes with desirable properties for use in DNA-based storage. Namely, these codes have balanced GC-content and can be reconstructed from few traces. Such codes are designed by exploiting the fact that the marker-based constructions can be instantiated with a large range of inner codes, and we can make the inner code satisfy stronger constraints than before.

3.1 A Simple Construction

Here, we provide a precise description of the encoder Enc for our code C and prove Theorem 1. For simplicity, we consider $d=\frac{1}{2}$ throughout. Let $\ell = 50 \log n$, and define two strings $M_0 = 0^\ell$ and $M_1 = 1^\ell$. Then, a marker M is a string of length $2\ell$ of the form $M=M_0 \| M_1 = 0^\ell | 1^\ell$. We also require an efficiently encodable and decodable inner code $C' \subseteq \{0, 1\}^{m+r}$ with encoder $Enc': \{0, 1\}^m \to \{0, 1\}^{m+r}$ where $m = \log^2 n$ and r is the redundancy, satisfying the following property.

Property 17. For all $c \in C$ and substrings s of c with $|s| = \sqrt{m}$, it holds that $w(s) \geq |s|/3$.

In other words, every codeword of C' has many 1's in all short enough sub strings. Such efficient codes exist with redundancy $r = O(\log m) = O(\log \log n)$. We provide a simple construction in Section 3.1.1.

Suppose we wish to encode an n-bit message $x \in \{0, 1\}^n$. The encoder Enc on input x proceeds through the following steps:

1. Split x into $n/\log^2 n$ blocks, each of length $\log^2 n$ such that:

$$x = x^{(1)} \| x^{(2)} \| \ldots \| x^{(n/\log^2 n)};$$

2. Encode each block x(i) under the inner code C' to obtain:

$$\bar{x}^{(i)} = Enc'(x^{(i)}) \in \{0, 1\}^{\log^2 n + r};$$

3. Set the encoding of x, denoted by Enc(x), to be:

$$Enc(x) = 1^\ell \| \bar{x}^{(1)} \| M \| \bar{x}^{(2)} \| M \| \ldots \| \bar{x}^{(n/\log^2 n)} \| 0^\ell.$$

We remark that the first run $1^\ell$ and the last run $0^\ell$ are superfluous, and are added only to make the analysis simpler. Computing Enc(x) from x and decoding x from Enc(x) can both be done efficiently if the inner code C' is efficiently encodable and decodable.

We now compute the redundancy of C. It is straightforward to see that $$|Enc(x)| \leq \frac{n}{\log^2 n}(|M| + |\bar{x}^{(1)}|) = n + O\left(\frac{n}{\log n}\right) + \frac{nr}{\log^2 n}. \quad (3)$$

As mentioned before, we have $r = O(\log \log n)$. Therefore, C can be made to have redundancy $$O\left(\frac{n}{\log n}\right).$$

In the remainder of this section, we prove Theorem 1 using C via a sequence of lemmas. For convenience, we restate the theorem below.

Theorem 18 (Theorem 1, restated). There is an efficient algorithm that recovers every $c \in C$ from $\exp(O(\log^{2/3} n))$ traces in time poly(n) with probability $1 - 1/\text{poly}(n)$.

To prove Theorem 1, we proceed in steps: First, we show that the markers M still contain long enough runs after they are sent through the deletion channel. Then, we show that no long runs of 0's originate from the sub-traces associated with each block. This implies that we can correctly identify the position of the "01" string of each marker in the trace. Finally, we show that we can apply the worst-case trace reconstruction algorithm from Lemma 10 to recover each block with high probability and with the desired number of traces.

We start by proving that the markers M still contain long runs after they are sent through the deletion channel.

Lemma 19. Let $0^{L_0} 1^{L_1}$ be the output of the deletion channel on input M. Then, $$Pr[L_0 > 10 \log n, L_1 > 0] \geq 1 - n^{-3}.$$

Proof. The result follows by a standard application of the Chernoff bound. More precisely, we have $E[L_0] = 25 \log n$, and hence $$Pr[L_0 \leq 10 \log n] = Pr[L_0 \leq E[L_0] - 15 \log n] \leq \exp\left(-\frac{15^2 \log^2 n}{2 E[L_0]}\right) \geq n^{-4}.$$

To conclude the proof, we note that $Pr[L_1 = 0] = 2^{-\ell} = n^{-50}$, and that the two events in question are independent.

We now show that no long runs of 0's originate from the sub-traces associated with each block.

Lemma 20. Let c∈C'. Then, a trace of c does not contain a run of 0's of length at least 10 log n with probability at least $1-n^3$.

Proof. Since c∈C', a run of 0's of length at least 10 log n in the trace of c requires that at least 10×(log n/3)−1 consecutive 1's are deleted in c. The probability that this happens for a fixed sequence of 10×(log n/3)−1 consecutive 1's is at most $n^{-33}$. Since there are at most $O(\log^2 n)$ such sequences in c, by the union bound, it follows that the desired probability is at most $n^{-3}$.

The next lemma follows immediately by combining Lemmas 19 and 20 with the union bound over the $n/\log^2 n$ blocks.

Lemma 21. Consider the following event E: We correctly identify the separation between the traces of $0^\ell$ and $1^\ell$ from every marker in the trace of Enc(x) by looking for all 1's that appear immediately after a run of at least 10 log n 0's.

Then, E happens with probability at least $1-n^{-2}$ over the randomness of the trace.

We are now ready to prove Theorem 1. Let E denote the event described in Lemma 21. Then, Lemma 21 implies that, conditioned on E happening, we can split a trace T of Enc(x) into $n/\log 2 n$ strings $T^{(1)}, \ldots, T^{n/\log 2n}$ satisfying the following:

1) The strings T(i) are independent;

2) Each string T(i) is distributed like a trace of $1^\ell \|x(i)\| 0^\ell$ conditioned on the high probability event E.

In fact, each string T(i) can be identified by looking for the (i−1)-th and i-th runs of 0 of length at least 10 log n in the trace T, and picking every bit in T immediately after the (i−1)-th run up to and including the i-th run.

Observe that $1^\ell \|x(i)\| 0^\ell$ has length $O(\log^2 n)$. Suppose that we have $t=\exp(O(\log n)^{2/3})$ independent traces $T_1, \ldots, T_t$ of Enc(x). Let $E_{au}$ denote the event that E holds for all $T_i$ simultaneously. Combining Lemma 21 with a union bound yields $$Pr[E_{all}] \geq 1-t/n^2 > 1-1/n \quad (4)$$

Fix some trace reconstruction algorithm A, and let $E_{indFail}^{(i)}$ denote the event that A fails to recover a fixed string $y(i)=1^\ell \|x(i)\| 0^\ell$ from t independent traces of y(i). Assuming that $E_{all}$ holds, the strings $T_1^{(i)}, \ldots, T_t^{(i)}$ are distributed as t independent traces of y(i), each also satisfying the conditions that the first run $1^\ell$ is not completely deleted, the last run $0^\ell$ has length at least 10 log n in the trace, and there is no run of 0's of length at least 10 log n in the trace of x(i). We denote the event that these conditions hold for all of the t of independent traces y(i) by $E_{split}^{(i)}$. Finally, we let $E_{fail}$ denote the event that we fail to recover Enc(x) from the t i.i.d. traces $T_1, \ldots, T_t$. Then, we have $$Pr[E_{fail}] \leq Pr[E_{fail}, E_{all}] + Pr[\neg E_{all}] \quad (5)$$

$$Pr[(\exists i:E_{indFail}^{(i)}), (\forall i:E_{split}^{(i)})] + Pr[\neg E_{all}]$$

$$\leq Pr[\exists i:E_{indFail}^{(i)}] + 1/n$$

$$\leq \sum_{i=1}^{n/\log^2 n} Pr[E_{indFail}^{(i)}] + 1/n. \quad (6)$$

The first equality follows from the discussion in the previous paragraph, the second inequality follows from (4), and the third inequality follows by the union bound. Instantiating A with the worst-case trace reconstruction algorithm from Lemma 10, we conclude from (6) that $$Pr[E_{fail}] \leq n \cdot \exp(-2 \log^2 n) + 1/n < 2/n,$$

As a result, we can successfully recover x from $\exp(O(\log n)^{2/3})$ traces of Enc(x) with probability at least $1-2/n$. To conclude the proof, we note that we can repeat the process O(log n) times and take the majority vote to boost the success probability to $1-1/p(n)$ for any fixed polynomial p of our choice. The total number of traces required is still $\exp(O(\log^{2/3} n))$. Since recovering each x(i) from the associated traces takes time $\exp(O(\log^{2/3} n))$ and the inner code C' has an efficient decoder, the whole procedure is efficient.

3.1.1 Instantiating the Inner Code

What remains to be done is to instantiate the inner code C' with the appropriate parameters and properties.

To this end, we present a simple construction of an efficiently encodable and decodable inner code C' with encoder Enc':$\{0, 1\}^m \rightarrow \{0, 1\}^{m+r}$ and redundancy $r=O(\log m)$. We can then obtain the desired code by setting $m=\log^2 n$. The starting point is the following result.

Lemma 22. Let g:$\{0, 1\}^t \rightarrow \{0, 1\}^m$ be the function whose existence is guaranteed by Lemma 8 with k=3w and $\epsilon=2^{-10w}$ for w=100 log m (hence t=O(log m)). Fix some $x \in \{0, 1\}^m$ and consider the random variable $Y=x+g(U_t)$. Then, with probability at least $1-2/m$, we have that Y satisfies the following property:

Property 23. $w(Y[a, a+w]) \geq 0.4w$ simultaneously for all $1 \leq a \leq m-w+1$.

Proof. Fix some a. Then, we have $$Pr[w(Y[a, a+w]) < 0.4w] = \sum_{y \in w(y) < 0.4w} Pr[Y[a, a+w) = y]$$

$$\leq \sum_{y \in w(y) < 0.4w} (2^{-w} + 2^{3w}\epsilon)$$

$$\leq 2^{wh(0.4)} \cdot 2^{-w+1}$$

$$\leq \frac{2}{m^2}.$$

The first inequality follows because Y is ε-almost k-wise independent, and the second inequality follows from a standard bound on the volume of the Hamming ball and the fact that $2^{3w}\epsilon < 2^{-w}$. Since there are at most m choices for a, by the union bound we conclude that Y fails to satisfy the desired property with probability at most $m \cdot 2/m^2 = 2/m$, as desired.

Given $x \in \{0, 1\}^m$, we evaluate Enc'(x) as follows: We iterate over all $z \in \{0, 1\}^t$ until we find z such that $y=x+g(z)$ satisfies $w(s[a, a+w]) \geq 0.4w$. Such a string z is known to exist by Lemma 22 and can be found in time poly(m) since t=O(log m). Then, we set Enc'(x)=z∥x+g(z).

Observe that the redundancy of C' is exactly $|z|=t=O(\log m)$, and that we have encoders and decoders for C' running in time poly(m) since t=O(log m). To see that C' satisfies the property required in this section, fix some substring s of Enc'(x) such that $|s| \geq \sqrt{m}$. Then, $w(s) \geq 0.4w \cdot |s|/w - t \geq 0.39|s|$ provided that m is large enough.

Finally, we remark that the code used in this marker-based construction is just an example of a viable inner code C'. Any structured family of codes satisfying Property 17 may be used instead, and one may envision adding more constraints to C', depending on the application constraints at hand. We exploit this fact in Sections 3.2 and 3.3. For example, in Section 3.3 we will require that C' is a code over {A, C, G, T} satisfying an analogue of Property 17 while also having balanced GC-content.

3.2 Adding a Second Level of Markers

In our next construction, we exploit the fact that the marker-based construction from Section 3.1 can be instantiated with a large range of inner codes to prove Theorem 2. To do so, we show that we can iterate the marker-based construction so that we can split a trace into even smaller sub-traces with high probability.

This leads to a code requiring fewer traces, but with a penalty in the redundancy. We restate Theorem 2 for convenience.

Theorem 24 (Theorem 2, restated). There exists an efficiently encodable code $C_0 \subseteq \{0,1\}^{n_0+r_0}$ with encoder $Enc_0: \{0,1\}^{n_0} \to \{0,1\}^{n_0+r_0}$ and redundancy $r_0 = O(n_0/\log \log n_0)$ that can be efficiently reconstructed from $\exp(O(\log \log n_0)^{2/3})$ traces with probability at least $1-2/n_0$.

As before, for simplicity we set $d=\frac{1}{2}$ throughout the section. We will use the same construction blueprint as in Section 3.1, except for the following differences:
1) We assume the n-bit message x belongs to a binary code $C_{Ham} \subseteq \{0,1\}^n$ with encoder $Enc_{Ham}: \{0,1\}^{n_0} \to \{0,1\}^n$ and relative (Hamming) distance$^2$ $30/\log^2 n_0$. In particular, we have $x = Enc_0(x_0)$ for some $x_0 \in \{0,1\}^{n_0}$.

Such efficiently encodable and decodable codes are known to exist with redundancy $$n - n_0 = O\left(n_0 \frac{\log \log n_0}{\log n_0}\right).$$

The reasons for using this encoding will be made clear later;
2) The inner code C' differs from the one used in Section 3.1.1.

If C denotes the code obtained via the reasoning of Section 3.1 and Enc corresponds to its encoder, then the encoder $Enc_0: \{0,1\}^{n_0} \to \{0,1\}^{n_0+r_0}$ for our final code $C_0$ is obtained by composing the encoders of $C_{Ham}$ and C, i.e., $$Enc_0 = Enc \circ Enc_{Ham}.$$

We proceed to describe the encoder Enc' for the inner code C' of C. Given $y \in \{0,1\}^m$, where $m = \log^2 n$, we split y into $m/\log^2 m$ blocks of length $\log^2 m$, $$y = y^{(1)} \| y^{(2)} \| \ldots \| y^{(m/\log^2 m)}.$$

Then, we take $C'' \subseteq \{0,1\}^{m'+r'}$ with encoder $Enc'': \{0,1\}^{m'} \to \{0,1\}^{m'+r'}$ as the efficiently encodable and decodable code constructed in Section 3.1.1 with message length $m' = \log^2 m$ and redundancy $r' = O(\log m') = O(\log \log m)$. For each i, we define $\bar{y}^{(i)} = Enc''(y^{(i)})$. Moreover, we let $\ell = 50 \log m$, and define the marker $M' = 0^\ell \| 1^\ell$. Then, we define Enc'(y) as $$Enc'(y) = M' \| \bar{y}^{(1)} \| M' \| \bar{y}^{(2)} \| M' \| \ldots \| M' \| \bar{y}^{(m/\log^2 m)} \| M'.$$

Observe that we can efficiently decode y from Enc'(y) provided that C" is efficiently decodable.

We first compute the redundancy of the inner code C' and the resulting code C obtained as in Section 3.1. We have $$|Enc'(y)| = m + \frac{m}{\log^2 m} \cdot (|M'| + O(\log \log m)) = m + O\left(\frac{m}{\log m}\right).$$

Thus, C' has redundancy $r = O(m/\log m)$. Plugging r into (3) and recalling that $m = \log^2 n$, we conclude that C has redundancy $$O\left(\frac{n}{\log n}\right) + O\left(\frac{n \log^2 n}{\log^2 n \cdot \log \log n}\right) = O\left(\frac{n}{\log \log n}\right).$$

As a result, since $$n = n_0 + O\left(n_0 \frac{\log \log n_0}{\log n_0}\right),$$

the code $C_0$ has redundancy $r_0 = O(n_0/\log \log n_0)$, as desired.

We now show that C' satisfies Property 17. First, we observe that C" satisfies Property 23 with m' in place of m. Then, since each M' has weight 0.5|M'|, we conclude that every substring s of Enc'(y) such that $|s| = \sqrt{m}$ satisfies $$w(s) \geq 0.4w \cdot |s|/w - \ell \geq 0.39|s|,$$

provided m is large enough, since $\ell = O(\log m)$. As a result, Lemma 21 holds for this choice of inner code, and we can hence focus solely on the trace reconstruction problem for strings of the form $$1^\ell \| Enc'(y) \| 1^\ell = 0^\ell \| M' \| \bar{y}^{(1)} \| M' \| \ldots \| M' \| \bar{y}^{(m/\log^2 m)} \| M' \| 0^\ell, \quad (7)$$

where $\ell = O(\log n) = O(\sqrt{m})$, and provided the number of traces used is significantly smaller than n. We now give a trace reconstruction algorithm for strings of the form (7) that requires $\exp(O(\log^{2/3} m)) = \exp(O(\log \log n_0)^{2/3})$ traces and time, and succeeds with probability at least $1 - 1/\text{poly}(m) = 1 - 1/\text{poly}(\log n_0)$.

We have the following two lemmas whose proofs are analogous to those of Lemmas 19 and 20 and hence omitted.

Lemma 25. Let $0^{L_0} 1^{L_1}$ be the output of the deletion channel on input M'. Then, $$Pr[L_0 > 10 \log m, L_1 > 0] \geq 1 - m^{-3}.$$

Lemma 26. Let $c \in C''$. Then, a trace of c does not contain a run of 0's of length at least $10 \log m$ with probability at least $1 - m^{-3}$.

Combining Lemmas 25 and 26 with the union bound leads to the following analogue of Lemma 21.

Lemma 27. Consider the following event E': We correctly identify the separation between the traces of $0^\ell$ and $1^\ell$ from every marker in the trace of Enc'(x) by looking for all 1's that appear immediately after a run of at least $10 \log m$ 0's.

Then, E' happens with probability at least $1 - m^{-2}$ over the randomness of the trace.

As in Section 3.1, Lemma 27 implies that, conditioned on E' happening for a trace T of $1^\ell \| Enc'(y) \| 0^\ell$, we can split T into independent sub-traces T(i) each distributed like a trace of $1^\ell \| Enc''(y(i)) \| 0^\ell$ conditioned on the high probability event E'.

Let A denote the worst-case trace reconstruction algorithm from Lemma 10 for strings of length $O(m') = O(\log^2 m)$, with failure probability at most $\exp(-\Omega(\log^2 m))$. A reasoning similar to that preceding (6) with Lemma 27 in place of Lemma 21, and the code C' designed in this section in place of C shows that, using algorithm A, we fail to recover Enc'(y) from $\exp(O(\log^{2/3} m))$ i.i.d. traces of $1^\ell \|\text{Enc}'(y)\|0^\ell$ with probability at most $$m \cdot \exp(-\Omega(\log^2 m)) + 1/m < 2/m. \quad (8)$$

Let A' denote the algorithm that recovers Enc'(y) from $\exp(O(\log^{2/3} m))$ i.i.d. traces of $1^\ell \|\text{Enc}'(y)\|0^\ell$ with failure probability at most 2/m as described above. We hope to instantiate (6) directly with A' to obtain the desired upper bound on the reconstruction failure probability for C. However, this approach does not produce a satisfactory result as the failure probability of A' is $2/m = 1/\text{poly}(\log n)$, which is too large to be used in the union bound.

Recall from Section 3.1 that, given $x \in \{0, 1\}^n$, the codeword Enc(x) of C is obtained by splitting x into $n/\log^2 n$ blocks $x^{(i)}$ and encoding each block with the encoder Enc' associated with C'. From the discussion in the previous paragraph, a fraction of blocks $x^{(i)}$ will be reconstructed with errors. Below we argue that this fraction is of size at most $10/\log^2 n_0$ with probability at least $1 - 2/n_0$. The reasoning is similar in spirit to that used to derive (5), and it suffices to complete the proof of Theorem 2. In fact, suppose we recovered $\tilde{x}$, which is a guess of x with at most a $(10/\log^2 n_0)$-fraction of incorrect blocks. In particular, the relative Hamming distance between x and $\tilde{x}$ is at most $10/\log^2 n_0$. Since the relative distance of $C_{Ham}$ is at least $30/\log^2 n_0$ and we assumed that $x \in C_{Ham}$, it follows that $\text{Dec}_{Ham}(\tilde{x}) = \text{Dec}_{Ham}(x) = x_0$.

Therefore, we conclude that we can recover the underlying message $x_0$ with probability at least $1 - 2/n_0$ from $\exp(O(\log^{2/3} m)) = \exp(O(\log \log n_0)^{2/3})$ i.i.d. traces of $\text{Enc}_0(x)$. This proves Theorem 2.

As the last step, we show that the fraction of bad blocks is small enough with high probability. Suppose that we have access to $t = \exp(O(\log^{2/3} m))$ i.i.d. traces $T_1, \ldots, T_t$ of Enc(x), where Enc is the encoder associated with C. Let E denote the event from Lemma 21, and let $E_{all}$ denote the event that E holds for all $T_i$ simultaneously. As before, assuming that $E_{all}$ holds, the strings $(T_i^{(i)}, \ldots, T_t^{(i)})_{1 \le i \le n/\log^2 n}$ are independent between all i, and each tuple of strings $T_1^{(i)}, \ldots, T_t^{(i)}$ is distributed as t independent traces of $1^\ell \text{Enc}'(x(i))\|0^\ell$, each $T_j^{(i)}$ also satisfying the conditions that the first run $1^\ell$ is not completely deleted, the last run $0^\ell$ has length at least $10 \log n$ in the trace, and no run of 0's has length at least $10 \log n$ in the trace of Enc'(x(i)). Denote the event that both these conditions hold for t independent traces of $1^\ell \|\text{Enc}'(x(i))\|0^\ell$ by $E_{split}^{(i)}$. Invoking the trace reconstruction algorithm A' defined above, let $I_{indFail}^{(i)}$ denote the indicator random variable of the event that A' fails to recover $1^\ell \|\text{Enc}'(x(i))\|0^\ell$ from t independent traces of $1^\ell \|\text{Enc}'(x(i))\|0^\ell$. Taking into account the previous discussion, we let $E_{fail}$ denote the probability that more than a $(10/\log^2 n_0)$-fraction of blocks x(i) is recovered with errors. Then, we have $$\Pr[E_{fail}] \le \Pr[E_{ind}, E_{all}] + \Pr[\neg E_{all}] \quad (9)$$

$$= \Pr\left[\sum_{i=1}^{n/\log^2 n} I_{indFail}^{(i)} > \frac{n}{\log^2 n} \cdot \frac{10}{\log^2 n_0}, \forall i : E_{split}^{(i)}\right] +$$

$$\Pr[\neg E_{all}]$$

$$\le \Pr\left[\sum_{i=1}^{n/\log^2 n} I_{indFail}^{(i)} > \frac{n}{\log^2 n} \cdot \frac{10}{\log^2 n_0}\right] + 1/n_0.$$

The first equality follows from the discussion in the previous paragraph, and the second inequality follows from Lemma 21 and the fact that $n > n_0$. Recalling (8), which asserts that the failure probability for A' is at most 2/m, shows that $$\Pr[I_{indFail}^{(i)}] \le 2/m = 2/\log^2 n < 2/\log^2 n_0$$

holds for every i. Since the $I_{indFail}^{(i)}$ are independent for all i, a standard application of the Chernoff bound yields the following lemma.

Lemma 28. We have $$\Pr\left[\sum_{i=1}^{n/\log^2 n} I_{indFail}^{(i)} > \frac{n}{\log^2 n} \cdot \frac{10}{\log^2 n_0}\right] \le n_0^{-10}.$$

We remark that the Chernoff bound yields a stronger upper bound than the one featured in Lemma 28. However, for simplicity we use a weaker upper bound that still suffices for our needs. Combining (9) with Lemma 28 allows us to conclude that $\Pr[E_{fail}] < 2/n_0$, as desired.

3.3 A Code for DNA-Based Data Storage Decodable from a Few Traces

We describe next how to adapt the ideas from Sections 3.1 and 3.2 in order to construct codes over the alphabet {A, C, G, T} that have balanced GC-content and provably require few traces for reconstruction. As already pointed out, strings with balanced GC-content are significantly easier to synthesize than their non-balanced counterparts. Therefore, constructions accommodating this constraint are well-suited for use in DNA-based data storage.

The constructions follow those outlined in Sections 3.1 and 3.2. The only modifications are the choice of markers and the definition of the inner code. We focus on discussing these changes and their properties within the setting of Section 3.1. The full argument and the extension for the two-level marker-based construction of Section 3.2 follow in a straightforward manner.

We first describe the modified markers. The marker M used throughout the section is of the form $M = (AC)^\ell \| (TG)^\ell$, where $\ell = 25 \log n$ and n is the message length. Observe that this marker has the same length as the original marker in Section 3.1. Moreover, M has balanced GC-content.

In order to proceed as in Section 3.1 we need to design an efficiently encodable and decodable inner code $C' \subseteq \{A, C, T, G\}^{m'}$ with balanced GC-content which satisfies a property analogous to Property 17.

Suppose that C' has encoder Enc': $\{0, 1\}^m \to \{A, C, T, G\}^{m'}$ and that m' = m/2 + r, where $m = \log^2 n$ as in Section 3.1 and r denotes the redundancy to be determined. Given the composition of M, the property we wish C' to satisfy is the following: Property 29. For all $c \in C'$ and substrings s of c with $|s| = \sqrt{m}$, it holds that at least $|s|/3$ symbols of s are T or G.

Similarly to Lemma 20, it can be shown that if C' satisfies Property 29, then with high probability a trace of $c \in C'$ will not contain long runs consisting only of symbols A and C. As a result, with high probability we can easily split a trace into many sub-traces associated with different blocks as in Section 3.1. This is accomplished by looking for all long substrings of the trace consisting only of A's and C's in the trace. The reason is that, with high probability, each such substring consists of the trace of an $(AC)^\ell$ substring from a marker M possibly with some extra symbols prepended. In that case we can correctly identify the separation between the traces of $(AC)^\ell$ and $(TG)^\ell$ in all markers by looking for the first T or G after every sufficiently long substring of A's and C's.

We proceed to describe the encoder Enc' of the inner code C' that has redundancy r=O(log m).

We combine the code from Section 3.1.1. along with a requirement of an efficiently encodable and decodable binary balanced code $C_1$ with encoder $Enc1:\{0,1\}^{m/2} \to \{0, 1\}^{m/2+r_1}$. Nearly-optimal constructions of such codes are known, and they have redundancy $r_1=O(\log m)$. Let $C_2 \subseteq \{0, 1\}^{m/2+r_2}$ denote the code from Section 3.1.1 with encoder $Enc1:\{0,1\}^{m/2} \to \{0,1\}^{m/2+r_2}$ and redundancy $r_2=O(\log m)$. By padding one of $C_1$ or $C_2$ appropriately, we may assume that $r_1=r_2=r$, i.e., that both codes have the same block length. We define the bijection $\Psi:\{0, 1\}^n \times \{0, 1\}^n \to \{A,C,G,T\}^n$ as $$\Psi(a, b)_i = \begin{cases} A, & \text{if } (a_i, b_i) = (0, 0), \\ T, & \text{if } (a_i, b_i) = (0, 1), \\ C, & \text{if } (a_i, b_i) = (1, 0), \\ G, & \text{if } (a_i, b_i) = (1, 1). \end{cases}$$

The code C' is defined via an encoding $Enc':\{0, 1\}^m \to \{A, C, G, T\}^{m/2+r}$ of the form $$Enc'(x)=\Psi(Enc_1(x^{(1)}),Enc_2(x^{(2)})),$$

where $x=x^{(1)} \| x^{(2)} \in \{0, 1\}^{m/2} \times \{0, 1\}^{m/2}$. It is clear that decoding x from Enc'(x) can be performed efficiently. We hence have the following lemma.

Lemma 30. The inner code C' has balanced GC-content and satisfies Property 29.

Proof Suppose that $c=\Psi(c_1, c_2)$, where $c_1 \in C_1$ and $c_2 \in C_2$. To see that c has balanced GC-content, note that the number of C's and G's in c equals the weight of $c_1$. We have $w(c_1)=|c_1|/2$ since $C_1$ is a balanced code, and hence c has balanced GC-content. To verify that C satisfies Property 29, note that the number of T's and G's within a sub string c[i,j] equals $w(c_2[i, j])$. Since $C_2$ satisfies Property 17, the proof follows.

Given Lemma 30, we can now proceed along the steps described in Section 3.1 by splitting a trace of C into many short sub-traces associated with different blocks, and then applying a worst-case trace reconstruction algorithm on each block. We remark that although the algorithm from Lemma 10 works for worst-case trace reconstruction over binary strings, it can be easily adapted for quaternary strings. In fact, if t traces suffice for a worst-case trace reconstruction algorithm to reconstruct a string in $\{0, 1\}$n with high probability, then a simple modification of this procedure recovers any quaternary string in $\{A, C, G, T\}^n$ with 2t traces. This is achieved by mapping the symbols in the first t traces over $\{A, C, G, T\}$ to traces over $\{0, 1\}$ according to, say, $A \to 0, C \to 0, G \to 1, T \to 1$, and the symbols in the last t traces according to $A \to 0, C \to 1, G \to 0, T \to 1$.

We can now run the binary worst-case algorithm on both sets of t traces, and recover the original string over $\{A, C, G, T\}$ from the two outputs.

Taking into account the previous discussion, applying the reasoning from Section 3.1 to the marker M and inner code C' defined in this section leads to Theorem 3, which we restate for completeness.

Theorem 31 (Theorem 3, restated). For every deletion probability d<1, there exists an efficiently encodable code $C \subseteq \{A, C, G, T\}$n+r with redundancy $r=O(n/\log n)$ and balanced GC-content that can be efficiently reconstructed from $\exp(O(\log n)^{2/3})$ traces.

Following the reasoning from Section 3.2 with the modified markers and C" instantiated with the inner code C' we designed in this section proves Theorem 4, which we also restate for completeness.

Theorem 32 (Theorem 4, restated). For every constant deletion probability d<1, there exists an efficiently encodable code $C \subseteq \{A, C, G, T\}$n+r with redundancy $r=O(n/\log \log n)$ and balanced GC-content that can be efficiently reconstructed from $\exp(O(\log \log n)^{2/3})$ traces.

Finally, two comments are in place regarding the choice of markers. First, the marker sequence $M=(AC)^\ell \| (TG)^\ell$ may lead to hairpin formations when single stranded DNA is used. Hairpins are doublestranded folds, but may be easily controlled through addition of urea or through temperature increase. Second, repeats such as marker repeats are undesirable as they may lead to issues during DNA synthesis. To mitigate this issue, one can alternate marker sequences. For example, two valid marker options are $(AC)^\ell \| (TG)^\ell$ and $(AG)^\ell \| (TC)^\ell$, and any other marker where the sets of symbols used in each side are disjoint and C and G do not appear in the same side is appropriate for use in the construction.

Note that alternating markers in turn requires alternating the inner codes used between markers. This can be accommodated in a straightforward manner. Suppose that the block x(i) precedes an $(AC)^\ell \| (TG)^\ell$ marker. Then, we encode x(i) as usual with Enc' as defined in this section. However, if x(i) precedes an $(AG)^\ell \| (TC)^\ell$ marker, then we encode x(i) by first computing Enc'(x(i)), and then swapping all G's and C's in the encoding. Observe that in both cases the encoding has balanced GC-content. Moreover, since C' satisfies Property 29, with high probability the trace of each block's encoding will not have long substrings containing only A's and C's (resp. A's and G's) before an $(AC)^\ell \| (TG)^\ell$ marker (resp. $(AG)^\ell \| (TC)^\ell$ marker).

As before, this means that, with high probability, we can correctly split the full trace into the relevant subtraces by alternately looking for long substrings composed of A's and C's only, and of A's and A's and G's only. In fact, the end of such long substrings corresponds to the beginning of the traces of the $(TG)^\ell$ and $(TC)^\ell$ substrings of the marker, respectively.

4. Reducing the Number of Traces for Small Constant Deletion Probability

In Section 3, we gave a construction of marker-based codes that require a few traces for reconstruction. A simple property of the inner code ensured that we can correctly identify all markers with high probability, effectively dividing the global trace into many independent, shorter traces. After this, we applied the worst-case trace reconstruction algorithm from Lemma 10 on each short trace in order to obtain the desired codes.

It seems plausible, however, that one could design the inner code more carefully so that many fewer traces are needed to recover the short codewords contained between the markers. This is the main problem we address in this section. We design a code that, when used as the inner code in the construction from Section 3, leads to an almost exponential reduction of the number of traces required for reconstruction with only a slight decrease in the code rate, provided that the deletion probability is a sufficiently small constant. The trace reconstruction algorithm we use is a variation of the algorithm for average-case trace reconstruction described elsewhere.

Our starting point is a low redundancy code with the property that it can be reconstructed from poly(n) traces. We discuss this construction in Section 4.1. Then, in Section 4.2 we show how to adapt this code so that it can be successfully used as an inner code in the marker-based construction introduced in Section 3.

4.1 Low Redundancy Codes Reconstructable from Polynomially Many Traces

In what follows, we prove Theorem 5. We restate the result for convenience.

Theorem 33 (Theorem 5, restated). For small enough deletion probability d, there exists an efficiently encodable code $C \subseteq \{0, 1\}^{n+r}$ with encoder Enc: $\{0, 1\}^n \to \{0, 1\}^{n+r}$ and redundancy $r=O(\log n)$ that can be efficiently reconstructed from poly(n) traces with probability at least $1-\exp(-n)$.

The code we construct to prove Theorem 5 will be the starting point for the proof of Theorem 6 in Section 4.2. Roughly speaking, our code encodes n-bit messages into codewords that are almost w-subsequence-unique for $w=O(\log n)$, in the sense that all but the first $O(\log n)$ bits of the codeword comprise a w-subsequence-unique string. This is possible because an $\epsilon$-almost k-wise independent random variable over $\{0, 1\}^n$ with the appropriate parameters is w-subsequence-unique with high probability. We make this statement rigorous in the following lemma. We note that the technique in the lemma below has already been used to obtain strings satisfying related properties, such as substring-uniqueness, with high probability.

Lemma 34. Let $g:\{0, 1\}^t \to \{0, 1\}^m$ be the function guaranteed by Lemma 8 with $k=3w$ and $\epsilon=2^{-10w}$ for $w=100 \log m$ (hence $t=O(\log m)$). Fix some $x \in \{0, 1\}^m$ and define the random variable $Y=x+g(U_t)$. Then, with probability at least $1-1/\text{poly}(m)$ it holds that Y is w-subsequence-unique.

Proof First, note that Y is $\epsilon$-almost k-wise independent. This proof follows along the same lines as the proof that a random string is w-subsequence-unique with high probability with a few simple modifications.

Without loss of generality, fix a and b such that $a<b$, and fix distinct indices $i_1, \ldots, i_w \in [b, \ldots, b+1.1w)$. For convenience, let $S=\{i_1, \ldots, i_w\}$, $S'=[b, b+1.1w)-S$, and $u=\min(a+w, b)$. Then, $$Pr[Y_S = Y[a, a+w]] = \qquad (10)$$

$$\sum_{y,y'} Pr[Y_S = Y[a, a+w], Y[a, u) = y, Y_{S'} = y'].$$

We now show that Y[a, u) and $Y_{S'}$ completely determine $Y_S$ under the constraint $Y_S=Y[a, a+w]$. This can be seen by induction. First, we must have $Y_{i_1}=Y_a$, and $Y_a$ is determined by Y[a, u) since $a<u$.

Now, suppose that $Y_{i_1}, \ldots, Y_{i_j}$ are determined by Y[a, u) and $Y_{S'}$. It must be the case that $Y_{i_{j+1}}=Y_{a+j}$. If $a+j<u$ or $a+j \in S'$, then $Y_{i_{j+1}}$ is determined by Y[a, u) or $Y_{S'}$, respectively. On the other hand, if $a+j \geq u$ and $a+j \notin S'$, then $Y_{a+j}=Y_{i_d}$ for some $d<j+1$. By the induction hypothesis, $Y_{i_d}$ is determined by Y[a, u) and $Y_{S'}$, and hence $Y_{i_{j+1}}$ is, too.

As a result, we conclude that there exists a string $\bar{y}=(\bar{y}_1, \ldots, \bar{y}_w)$ completely determined by y and y' such that $$Pr[Y_S = Y[a,a+w], Y[a,u)=y, Y_{S'}=y'] = Pr[Y_S = \bar{y}, Y[a,u)=y, Y_{S'}=y']. \qquad (11)$$

Since Y is $\epsilon$-almost 3w-wise independent and fewer than 3w coordinates are fixed, we have $$Pr[Y_S = \bar{y}, Y[a,u)=y, Y_{S'}=y'] \leq 2^{-1.1w-(u-a)}+2^{3w}\epsilon \qquad (12)$$

for all y and y'. Combining (10), (11), and (12), we conclude that $$Pr[Y_S = Y[a, a+w]] \leq 2^{u-v} \cdot 2^{0.1w}(2^{-1.1w-(a-u)}+2^{3w}\epsilon) \leq 2^{-w} + 2^{4.1w}\epsilon \leq 2^{-w+1},$$

since $u-a \leq w$ and $\epsilon=2^{-10w}$. Since there are $$\binom{1.1w}{w}$$

choices for S for each pair (a, b) and fewer than $m^2$ possible pairs (a, b), the probability that Y is not w-subsequence-unique is at most $$m^2 \binom{1.1w}{w} 2^{-w+1} = n^2 \binom{1.1w}{w} 2^{-w+1}$$

$$\leq m^2 (11e)^{0.1w} 2^{-w+1}$$

$$\leq 2m^2 (1.415)^{-w}$$

$$\leq m^{-48},$$

as desired.

Lemma 34 naturally leads to a simple, efficient candidate construction of the encoder Enc: Given $x \in \{0, 1\}^n$, we first iterate over all $z \in \{0, 1\}^t$ until we find z such that $x+g(z)$ is w-subsequence-unique. Most strings z satisfy this, according to Lemma 34. Moreover, since $t=O(\log n)$, we can iterate over all such z in time poly(n), and verify whether $x+g(z)$ is w-subsequence-unique for each z in poly(n) time. To recover x from $x+g(z)$ we need to provide z to the receiver. Therefore, the encoder Enc for C maps a message $x \in \{0, 1\}^n$ to the codeword $$\text{Enc}(x) = z \| x+g(z) \in \{0, 1\}^{n+t}, \qquad (13)$$

where z is the first string (in lexicographic order) such that $x+g(z)$ is w-subsequence-unique. Observe that the redundancy of C is exactly $t=O(\log n)$.

4.1.1 the Trace Reconstruction Algorithm

In this section, we describe an efficient trace reconstruction algorithm for C that works whenever the deletion probability is a small enough constant, thus proving Theorem 5. This algorithm works very similarly to the one described in Section 2.4.2. As before, we shall set $w=100 \log n$, $v=w/d=O(\log n)$ and $j=(v-0.1w)(1-3d)=O(\log n)$. Given a codeword $c=\text{Enc}(x)=+g(z)$, we proceed as follows:

First, we apply the algorithm from Lemma 14 to recover z and the first $2v+w=O(\log n)$ bits of $y=x+g(z)$ with poly(n) traces (repeating the process O(n) times if necessary) and success probability $1-\exp(-\Omega(n))$. Now, suppose that we know $y_1, \ldots, y_{i-1}$ for $i-1 \geq 2v+w$. We show how to find)), with probability $1-\exp(-\Omega(n))$ from poly(n) traces, which concludes the proof of Theorem 5.

Let T denote a trace of c. As in Section 2.4.2, we will look for a matching of y[i-v-w, i-v) within T. However, we shall discard matchings that occur too early in T. More precisely, suppose that y[i-v-w, i-v) is matched with T [u-w, u). We call such a matching good if $u-w>|z|$. If T does not contain a good matching of y[i-v-w, i-v), we discard it. Otherwise, if the first good matching occurs at T [u-w, u), we let V=T

[u, •] and discard the remaining bits of T. Our observations so far are summarized in the following lemmas.

Lemma 35. For d small enough, the probability that a good matching occurs in T is at least $2^{-(w+1)}$.

Proof. First, observe that the probability that no bit in y[i−v−w, i−v) is deleted is exactly $(1-d)^w \geq 2^{-w}$.

Given this, suppose that y[i−v−w, i−v) shows up in positions T [U−w, U). Then, the probability that the given matching is good equals Pr[U>|z|+w], and |z|+w≤Cw for a fixed constant C>0, since |z|=O(log n). Note that we may assume i−v−w≥v=w/d since we have already learned the first 2v+w bits of y. We may also choose d<1/10 small enough such that v>Cw. Then, we have $$Pr[U \leq |z|+w] \leq Pr[Bin(2Cw, 1-d) \leq Cw] < \frac{1}{2},$$

where the last inequality follows from an application of the Chernoff bound. Concluding, the trace T contains a good matching with probability at least $\frac{1}{2} \cdot 2^{-w} = 2^{-(w+1)}$.

Lemma 36. The probability that the last bit of a good matching in T does not come from y[i−v, i−v+0.1w) is at most $nd^{-w/100} \leq 2^{-100w}$ if d is small enough.

Proof. The probability that the event in question happens is at most the probability that more than 0.1w bits are deleted from some substring y[b, b+1.1w). To see this, first note that the bits in a good matching must come from y. If at most 0.1w bits are deleted from every substring y[b, b+1.1w), then the w bits of the good matching in T for y[i−v−w, i−v) must be a subsequence of y[b, b+1.1w) for some b, which means y[i−v−w, i−v) appears as a subsequence of y[b, b+1.1w). Since y is w-subsequence-unique, for this to happen we must have b≤i−v−w and b+1.1w≥i−v. Now suppose that the last bit of the good matching in T does not come from y[i−v, i−v+0.1w). Then, it must be the case that y[i−v−w, i−v) is a subsequence of y[b, i−v−1). Since i−v−1<i−v, this violates the w-subsequence-uniqueness property of y.

For a fixed b, the probability that more than 0.1w bits are deleted from y[b, b+1.1w) is at most $d^{-w/100}$ for d small enough. The result then follows by a union bound, since there are fewer than n choices for b.

Let $E_{good}$ denote the event that a good matching occurs in T. From Lemma 35 and the fact that we can efficiently check whether $E_{good}$ occurred for T, it follows that we can efficiently estimate $$Pr[V_j=1 | E_{good}]$$

to within an error of, say, $2^{-100w}$ from poly(n) traces, with probability at least $1-\exp(-\Omega(n))$. Then, we proceed similarly to Section 2.4.2. Let R be the random variable denoting the coordinate in y of the last bit appearing in the good matching within T We may then write $$Pr[V_j = 1 | E_{good}] = \sum_{r=1}^{n} Pr[R = r | E_{good}] Pr[V_j = 1 | R = r, E_{good}]$$

$$= \epsilon_i(c) + \sum_{r=i-v}^{i-v+0.1w} Pr[R = r | E_{good}] Pr[V_j = 1 | R = r]$$

for $0 \leq \epsilon_i(c) \leq 2^{-100w}$, by Lemma 36. The second equality follows because, once R=r is fixed, V does not depend on whether $E_{good}$ occurs or not, but only depends on the traces of z and y[1, r]. Therefore, as in (1) and (2) we have $$y_s = 0 \Rightarrow Pr[V_j = 1 | E_{good}] \leq \qquad (14)$$

$$\epsilon_i(c) + \sum_{r=i-o}^{i-o+0.1w} Pr[R = r | E_{good}] \sum_{\ell=w+1}^{\ell-1} P(\ell - r_s, j) s_\ell +$$

$$\frac{1}{2} \sum_{r=y-c}^{i-r+0.1w} Pr[R = r | E_{good}] P(i - r, j)$$

and $$y_i = 1 \Rightarrow Pr[V_j = 1 | E_{good}] \geq \qquad (15)$$

$$\epsilon_i(c) + \sum_{r=i-v}^{i-v+0.1w} Pr[R = r | E_{good}] \sum_{\ell=r+1}^{\ell-1} P(\ell - r, j) s_\ell +$$

$$\frac{1}{2} \sum_{r=i-v}^{i-v+0.1w} Pr[R = r | E_{good}] P(i - r, j).$$

Similarly to what was done in Section 2.4.2, since i−r≤v and v=w/d, the second part of Lemma 13 implies that P(1−r, j)>$2^{-9w}$. Combining this result with Lemma 36 shows that the gap between the right hand sides of (14) and (15) is at least $2^{-(9w+1)}$. Each term $Pr[R=r|E_{good}]$ can be approximated to within an error of $2^{-90w}$ with probability at least 1−exp(−Ω(n)) in time poly(n). This is accomplished by first using z and the values $y_1, \ldots, y_{i-1}$ that we have already recovered to estimate $Pr[R=r|E_{good}, R<i]$ to within a small enough error and with high probability. Then, the fact that $Pr[R<i|E_{good}] \geq 1-2^{-100w}$ and Lemma 36 imply that $$|Pr[R=r|E_{good}] - Pr[R=r|E_{good}, R<i]| \leq 2 \cdot 2^{-100w},$$

which in turn implies a good enough approximation for $Pr[R=r|E_{good}]$.

Since we know $y_1, \ldots, y_{i-1}$, the discussion above suggests that we can approximate the right hand side of (14) and (15) to within an error of $$2^{-100w} + n^2 \cdot 2^{-90w} \leq 2^{-80w}$$

with high probability. As already mentioned, we can estimate $Pr[V_j=1|E_{good}]$ to within error $2^{-100w}$ from poly(n) traces in time poly(n) with probability at least 1−exp(−Ω(n)). Consequently, with probability 1−exp(−Ω(n)) we can recover $y_i$ correctly from poly(n) traces, where the degree of this polynomial is independent of i. The success probability can be made at least $1-\exp(-C_n)$ for any fixed constant C of our choice by repeating the process O(n) times and taking the majority vote. Overall, we must recover fewer than n positions of y, and each position requires poly(n) traces, where the degree of this polynomial is independent of the position of the bit. As a result, the total number of traces required is poly(n) and the overall success probability is 1−1/poly(n). This proves Theorem 5.

4.2 Using the Code within a Marker-Based Construction

Next, we combine the constructions from Sections 3 and 4.1 with some additional modifications in order to prove Theorem 6, which we restate here.

Theorem 37 (Theorem 6, restated). For small enough deletion probability, there exists an efficiently encodable code C with encoder Enc:{0, 1}n→{0, 1}n+r and redundancy r=O(n/log n) that can be efficiently reconstructed from poly(log n) traces with probability 1−1/poly(n).

The basic idea is that we would like to use the code designed in Section 4.1 as the inner code C' for the construction of C in Section 3. Then, we could apply the trace reconstruction algorithm from Section 4.1.1 on each sub-trace and mitigate the use of worst-case trace reconstruction algorithms. This idea includes some modifications to the code from Section 4.1 to allow the construction to go through.

The first issue we have to address is for the inner code C' to satisfy Property 17. If this property holds, then the reasoning of Section 3 implies that we can focus on the trace reconstruction problem for strings of the form $$1^{\ell} \|c\| 0^{\ell}, \tag{16}$$

where $c \in C'$ has length $O(\log^2 n)$ and $\ell = O(\log n)$, as long as we use a sub-polynomial number of traces in n. From here onwards we focus solely on this setting. If we were to directly apply the trace reconstruction algorithm from Section 4.1.1, we would run into a problem. For the aforementioned algorithm to work, we need to bootstrap it by recovering the first few bits of c using the procedure described in Lemma 14. However, in this case c only appears after a run of length $\ell = O(\log n)$. Even though we know the previous bits, we still require poly(n) traces to recover the first bit of c in this way, which is not acceptable as we want to use poly(log n) traces. Consequently, we need an alternative bootstrapping method. Another issue we need to resolve is that the reconstruction algorithm from Section 4.1.1 assumed that all but the first few bits of c lead to a subsequence-unique string. However, this is not the case here, as we must deal with a string of the form $c \| \ 0^{\ell}$.

Before we proceed to describe a modified version of our code from Section 4.1 that avoids the issues raised above, we first prove the following lemma.

Lemma 38. Let $g: \{0, 1\}^t \to \{0, 1\}^m$ be the function guaranteed by Lemma 8 with $k=3w$ and $\epsilon = 2^{-10w}$ for $w=100 \log m$ (hence $t=O(\log m)$). For arbitrary $\ell$ and $x \in \{0, 1\}^m$, define the random variable $Y = x + g(U_t) \| \ 0^{\ell}$. Then, with probability at least $1 - 1/\text{poly}(m)$ we have that Y satisfies the following property.

Property 39. For any a and b such that $a + w \leq \min(m+1, b)$, we have that $Y[a, a+w)$ is not a subsequence of $Y[b, b+1.1w)$.

Proof. Fix a pair (a, b) satisfying $a + w \leq \min(m+1, b)$ and let $S \subseteq [b, b+1.1w)$ be a set of size w. Let $u = \min(m+1, b+1.1w)$. Then, we have $$Pr[Y[a, a+w) = Y_S] = \sum_y Pr[Y[a, a+w) = Y_S, Y[b, u) = y, Y[m+1, b+1.1w) = (0, \ldots, 0)].$$

Observing that $Y_S$ is completely determined by $Y[b, u)$ and $Y[m+1, b+1.1w)$ and that $Y[m+1, b+1.1w)$ is fixed, we have $$Pr[Y[a, a+w) = Y_S] = \sum_y Pr[Y[a, a+w) = y', Y[b, u) = y]$$

for some y' determined by y. Since $x + g(U_t)$ is $\epsilon$-almost 3w-wise independent and fewer than 3w coordinates are fixed, we have $$Pr[Y[a,a+w)=y', Y[b,u)=y] \leq 2^{-w-(u-b)} + 2^{3w} \epsilon.$$

Therefore, it follows that $$Pr[Y[a,a+w)=Y_S] \leq 2^{u-b}(2^{-w-(u-b)} + 2^{3w}\epsilon) \leq 2^{-w} + 2^{4.1w}\epsilon \leq 2^{-w+1}.$$

Since there are fewer than $m^3$ choices for pairs (a, b) and $$\binom{1.1w}{w}$$

choices for S, from the union bound, we conclude similarly to what we did in the proof of Lemma 34 that the probability that the desired event does not happen is at most $$m^3 \binom{1.1w}{w} 2^{-w+1} \leq m^{-45}.$$

Intuitively, Lemma 38 guarantees that $x + g(U_t)$ satisfies a stronger form of subsequence-uniqueness with high probability. In fact, not only is $x + g(U_t)$ w-subsequence-unique with high probability based on Lemma 34, but also is it impossible to find a substring of $x + g(U_t)$ that is a subsequence of $x + g(U_t) \| 0^{\ell}$ elsewhere.

We are now ready to describe our modified inner code C' with encoder $\text{Enc}': \{0, 1\}^m \to \{0, 1\}^{m+r'}$. On an input message $x \in \{0, 1\}^m$, Enc' operates as follows:

1. Set $x' = 0^{\ell'} \| x$ for $\ell' = 10\ell = O(\sqrt{m})$. Let $m' = |x'|$ and set $w = 100 \log m'$;
2. Iterate over all $z \in \{0, 1\}^t$ for $t = O(\log m') = O(\log m)$ until a z such that $x' + g(z)$ is w-subsequence unique and simultaneously satisfies Properties 23 and 39 is found. Such a string z is guaranteed to exist because all such properties hold for $x' + g(U_t)$ with probability $1 - o(1)$ (see Lemmas 22, 34, and 38). Moreover, whether $x' + g(z)$ satisfies all three properties can be checked in time poly(m);
3. Obtain z' from z by setting $z' = \text{Enc}_{edit}(0 \| z)$, where $\text{Enc}_{edit}$ is the encoder of the systematic code $C_{edit}$ from Lemma 9 robust against $|z|/2$ edit errors and with redundancy $O(|z|) = O(\log m)$. Here, d is assumed to be a small enough constant so that $5d|z'| < |z|/2$, i.e., $C_{edit}$ can correct a 5d-fraction of edit errors in z'. This is possible because $|z'| = O(|z|)$;
4. Define $\text{Enc}'(x) = z' \| x' + g(z) = z' \| y'$.

For a given message $x \in \{0, 1\}^m$, we can compute $\text{Enc}'(x)$ in time poly(m). Furthermore, recalling that $m = \log^2 n$ in the construction of Section 3.1, the redundancy of C' is $$r' = |z'| + \ell' = O(\log m + \sqrt{m}) = O(\sqrt{m}) = O(\log n).$$

If we use C' as the inner code in the construction of C from Section 3.1, then according to (3) we obtain an overall redundancy $$r = O\left(\frac{n}{\log n}\right)$$

for C, as desired. It is also easy to see that C' satisfies Property 17. By the choice of z, we have $w(y' [a, a+w)) \geq 0.4w$ for every a and $w = 100 \log m'$. Therefore, for any substring s such that $|s| = \sqrt{m}$ we have $$w(s) \geq 0.4|x| - |z'| \geq 0.39|s|$$

provided m is large enough, since $|z'| = O(\log m)$. As a result, the reasoning used in Section 3.1 applies to this choice of C'. To prove Theorem 6, it remains to give a trace reconstruction algorithm to recover strings of the form $1^\ell \|\text{Enc}'(x)\| 0^\ell$ from poly(m)=poly(log n) traces with probability, say, $1-n^{-10}$.

To address the problem, suppose we already have such an algorithm, and call it A. Recall (6) and the definition of the event $E_{indFail}^{(i)}$ from Section 3.1. Instantiating $E_{indFail}^{(i)}$ with algorithm A leads to the bound $\Pr[E_{indFail}^{(i)}] \leq n^{-10}$, for all i. Combining this observation with (6) allows us to conclude that the probability that we successfully recover $c \in C$ from poly(log n) i.i.d. traces of c is at least $1^{-2/n}$. Similarly to Section 3.1, we can boost the success probability to $1-1/p(n)$ for any fixed polynomial of our choice by repeating the process O(log n) times and by taking a majority vote.

4.2.1 the Trace Reconstruction Algorithm

Next, we analyze an algorithm for recovering strings of the form $1^\ell \text{Enc}'(x) \| 0^\ell$ from poly(m)=poly(log n) traces with probability $1-1/\text{poly}(n)$. As discussed before, we proceed by adapting the algorithm from Section 4.1.1, which in turn is a modified version of the algorithm from Section 2.4.2.

The main difference between the current and the two previously discussed settings is that the original bootstrapping technique cannot be applied, as Enc'(x) is enclosed by two long runs. We start by showing that the structure of Enc' allows for a simple alternative bootstrapping method.

Recall that c=Enc'(x)=z'∥y', where y'=x'+g(z) and the first $O(\sqrt{m})$ bits of x' are zero. Therefore, if we can recover z from a few traces of $1^\ell \|c\| 0^\ell$, then we can recover the first $O(\sqrt{m})$ bits of y', which suffices for bootstrapping, by simply computing g(z). The following lemma states that we can recover z with high probability from O(log n) traces.

Lemma 40. There is an algorithm that recovers z from O(log n) traces of $1^\ell \|c\| 0^\ell$ with probability at least $1-n^{-10}$.

Proof. We begin by recalling that $z'=\text{Enc}_{edit}(0\|z)$, and that $C_{edit}$ is systematic. This means $z'_1=0$, and so with probability $1-d$, the first 0 appearing in the trace will correspond to $z'_1$.

Given a trace T of $1^\ell \|c\| 0^\ell$, we proceed as follows: Let u denote the position of the first 0 in T. Then, we take $\tilde{z}=T[u, u+(1-d)|z'|]$, feed $\tilde{z}$ into $\text{Dec}_{edit}$, and let the corresponding output be our guess for z. The probability that this procedure fails to yield z is at most the probability that $z'_1$ was deleted, plus the probability that $\tilde{z}$ is too far away in edit distance from z' given that $z'_1$ was not deleted. We proceed to bound both probabilities. First, the probability that $z'_1$ is deleted is exactly d. Second, we assume $z'_1$ is not deleted and let L denote the length of the trace of $z'[2, \bullet]$ within T. We have $E[L]=(1-d)(|z'|-1)$. Therefore, a Chernoff bound gives $$Pr[L \geq (1-3d)(|z'|-1)] \leq \exp\left(-\frac{2d^2}{1-d}(|z'|-1)\right).$$

Since d is a constant and $|z'|=\Theta(\log m)$, we conclude that for m large enough, we have $$Pr[|L-(1-d)(|z'|-1)| \geq 2d(|z'|-1)] < 1/5.$$

As a result, with probability at least ⅘ we have that $\tilde{z}$ is within edit distance $5d|z'|<|z|/2$ from z'. If this distance condition holds, then $\text{Dec}_{edit}(\tilde{z})=z$.

In summary, the procedure fails to return z with probability at most $d+1/5<1/4$ if d is small enough. Repeating this procedure O(log n) times and taking the majority vote ensures via a Chernoff bound that we can recover z from O(log n) traces with success probability at least $1-1/p(n)$, for p any choice of a fixed polynomial.

Once z has been recovered, the bits of $1^\ell \|c\| 0^\ell = 1^\ell \|z'\|y'\| 0^\ell$ are known up to and including the first $\ell' = O(\sqrt{m})$ bits of y'. Our last task is to recover the remaining bits of y', and given that we have sufficiently many initial bits from y' we may to this end use the ideas from Section 4.1.1. The differences with respect to Section 4.1.1 are the following:

1) Instead of y, we use $y''=y'\| 0^\ell$;
2) We are only interested in recovering $y''_i$ for $\ell' < i \leq |y'|$, since we already know all other bits of y'';
3) We change the threshold used to declare that a matching is good: In this case, if T is a trace of $1^\ell \|c\| 0^\ell$ and y'' [i−v−w, i−v] is matched with T [u−w, u], then the matching is said to be good if $u-w > \ell + |z'|$. This change ensures that the bits in a good matching always come from $y''=y'\| 0^\ell$.

Two key lemmas now follow from the previous discussion. Their statements and proofs are similar to the ones of Lemmas 35 and 36 from Section 4.1.1, respectively, and we hence only discuss relevant differences. Henceforth, we use T to denote a trace of $1^\ell \|c\| 0^\ell$.

Lemma 41. The probability that a good matching occurs in T is at least $2^{-(w+1)}$.

Lemma 42. For $\ell' < i \leq [|y'|$, the probability that the last bit of a good matching in T does not come from y''[i−v, i−v+0.1w] is at most $nd^{-w/100} \leq 2^{-100w}$ if d is small enough.

Proof. Similarly to the proof of Lemma 36, the probability of the event in the statement of the lemma is upper bounded by the probability that more than 0.1w bits are deleted from some substring y'' [b, b+1.1w).

We explain next why this is true. First, note that the bits in a good matching must come from y''. Suppose that at most 0.1w bits are deleted from every substring y'' [b, b+1.1w). Then, y'' [i−v−w, i−v) must be a subsequence of y'' [b, b+1.1w) for some $1 \leq b \leq |y''| - 1.1w$. We distinguish two cases:

1) $b+1.1w > |y'|$:

Recalling that v=w/d, we have $i-v \leq |y'|-w/d \leq |y'|-1.1w < \min(|y'|+1, b)$, and so Property 39 holds for y'' [i−v−w, i−v). Therefore, y'' [i−v−w, i−v) cannot be a subsequence of y'' [b, b+1.1w) for any b such that $b+1.1w > |y'|+1$. Consequently, we only need to consider values of b such that $b+1.1w \leq |y'|$;

2) $b+1.1w \leq |y'|$:

Since y' is w-subsequence-unique, we must have $b \leq i-v-w$ and $b+1.1w \geq i-v$. This implies the desired result as in the proof of Lemma 36;

The remainder of the proof follows along the lines of the proof of Lemma 36.

Lemmas 41 and 42 imply that we can recover y''$_i$ with probability $1-1/\text{poly}(n)$ via the same reasoning of Section 4.1.1 with the small differences described above. The number of traces required to recover y''$_i$ is polynomial in the length of $1^\ell \|c\|c0^\ell$, which equals $$2^\ell + |z'| + |y'| = O(\sqrt{m} + \log m + m) = O(m).$$

Since $m = \log^2 n$, it follows that we can recover y'$_i$ with probability $1-1/\text{poly}(n)$ from poly(log n) traces. In particular, the success probability can be assumed to be at least $1-1/p(n)$ for a fixed polynomial of our choice since we can repeat the process O(log n) times and take the majority vote while still requiring poly(log n) traces. Since Lemma 40 asserts that O(log n) traces suffice to recover z with high probability, and we need to recover $m=\log^2 n$ bits of $y''$, we overall require poly(log n) traces to recover $1^{l'}\|c\|0^{l'}$ with probability $1-1/\text{poly}(n)$. This concludes the proof of Theorem 6.

5. Example DNA-Based Sequencing Systems

FIG. 1 illustrates a DNA-based sequencing system 100, according to an example embodiment. The DNA-based sequencing system 100 includes a DNA sequencer 110 and a controller 120. The controller 120 could include, for example, one or more processors and at least one memory. The controller 120 is configured to carry out certain operations. The operations include receiving a message 130 having a message length n bits. The operations also include partitioning the message 130 into a plurality of blocks with a maximum block length of $O(\log^2 n)$. The operations additionally include encoding each block to provide a plurality of encoded blocks. The operations yet further include inserting unique markers between the encoded blocks so as to form an encoded message. The markers each have a minimum marker length $O(\log n)$. The operations additionally include causing the DNA sequencer to synthesize a nucleotide sequence 140 that includes the encoded message.

In some embodiments, the operation of encoding each block could include encoding the blocks according to an inner code. The inner code could include, for example, an alphabet consisting of {adenine (A), cytosine (C), guanine (G), and thymine (T)}.

In various embodiments, each unique marker could be of the form $M=(AC)^l\|(TG)^l$, where $l=25 \log n$.

In some embodiments, the encoded blocks could include approximately 50% guanine and cytosine content.

In some examples, the operations could additionally include further partitioning each block into a plurality of subblocks and inserting a second level of markers between each subblock. In such scenarios, the second level of markers could be different than the unique markers.

The memory devices described herein may include a non-transitory computer-readable medium, such as, but not limited to, read-only memory (ROM), programmable read-only memory (PROM), erasable programmable read-only memory (EPROM), electrically erasable programmable read-only memory (EEPROM), non-volatile random-access memory (e.g., flash memory), a solid state drive (SSD), a hard disk drive (HDD), a Compact Disc (CD), a Digital Video Disk (DVD), a digital tape, read/write (R/W) CDs, R/W DVDs, etc.

6. Example DNA-Based Readout Systems

Figure 2:
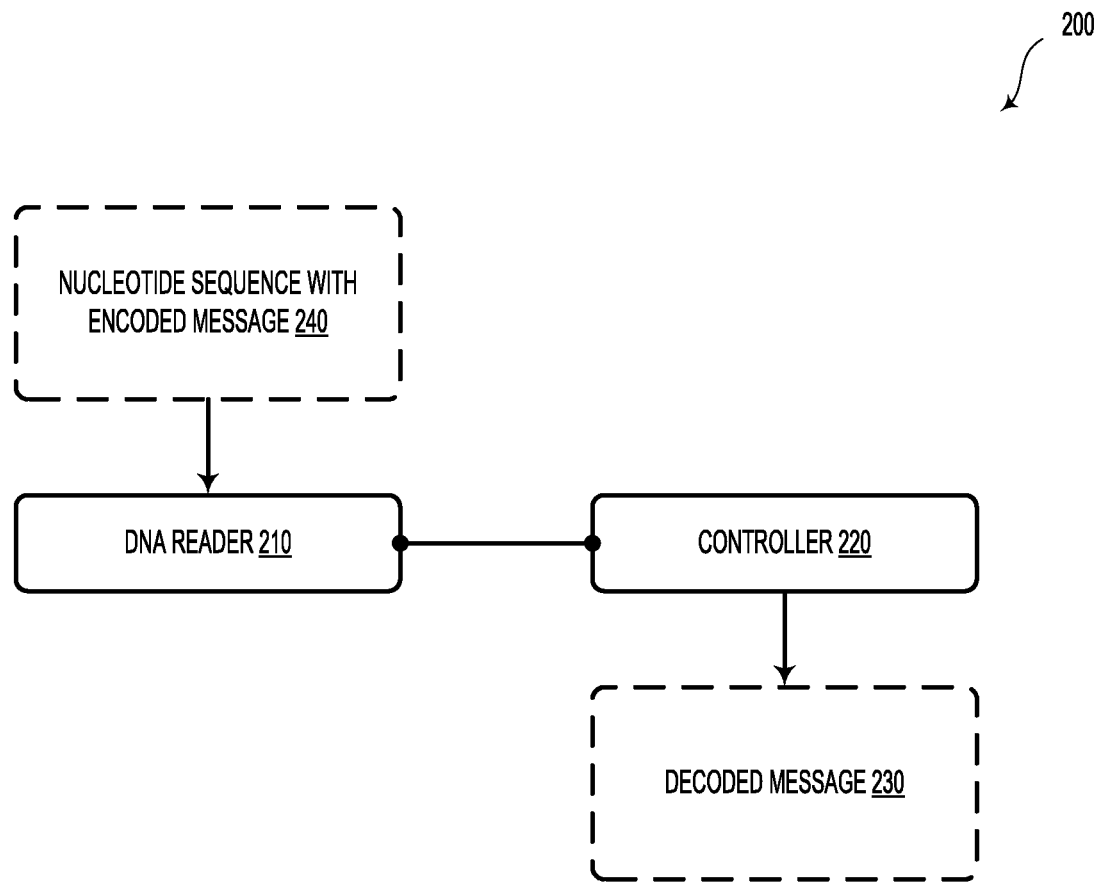
FIG. 2 illustrates a DNA-based readout system, according to an example embodiment.

FIG. 2 illustrates a DNA-based readout system 200, according to an example embodiment. The DNA-based readout system 200 includes a DNA reader 210 and a controller 220. The controller 220 could include, for example, one or more processors and at least one memory. The controller 220 is configured to carry out certain operations. For example, the operations could include receiving, at the DNA reader 210, a nucleotide sequence 240.

The operations include reading the nucleotide sequence 140 based on an alphabet consisting of {adenine (A), cytosine (C), guanine (G), and thymine (T)} and determining positions of unique markers between a plurality of encoded blocks in the nucleotide sequence 140.

The operations additionally include decoding each encoded block of the plurality of encoded blocks according to an inner code, so as to form a plurality of decoded blocks.

The operations include appending the decoded blocks to one another to provide a decoded message 230 with message length n bits.

In various embodiments, each unique marker could be of the form $M=(AC)^l\|(TG)^l$, where $l=25 \log n$.

In some embodiments, the encoded blocks could include of approximately 50% guanine and cytosine content.

In example embodiments, the operation of encoding each block could include encoding each block according to a Hamming encoding with a relative Hamming distance.

7. Example Methods

Figure 3:
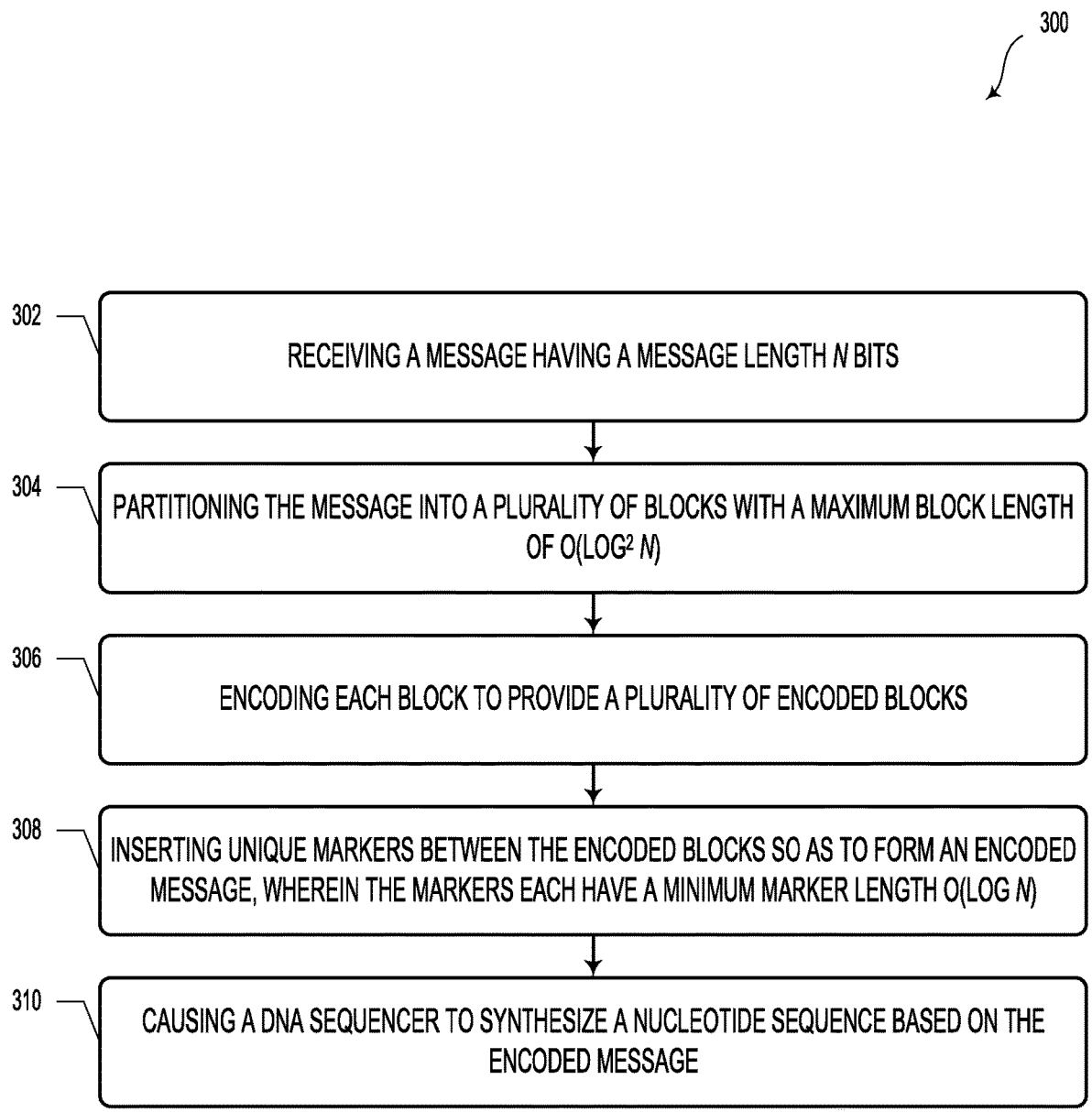
FIG. 3 illustrates a method, according to an example embodiment.

FIG. 3 illustrates a method 300, according to an example embodiment. It will be understood that the method 300 may include fewer or more steps or blocks than those expressly illustrated or otherwise disclosed herein. Furthermore, respective steps or blocks of method 300 may be performed in any order and each step or block may be performed one or more times. In some embodiments, some or all of the blocks or steps of method 300 may be carried out by a DNA-based sequencing system (e.g., DNA-based sequencing system 100). It will be understood that other scenarios are possible and contemplated within the context of the present disclosure.

Block 302 includes receiving a message (e.g., message 130) having a message length n bits;

Block 304 includes partitioning the message into a plurality of blocks with a maximum block length of $O(\log^2 n)$.

Block 306 includes encoding each block to provide a plurality of encoded blocks.

Block 308 includes inserting unique markers between the encoded blocks so as to form an encoded message. The markers each have a minimum marker length $O(\log n)$.

Block 310 includes causing a DNA sequencer (e.g., DNA sequencer 110) to synthesize a nucleotide sequence (e.g., nucleotide sequence 140) based on the encoded message.

In some embodiments, encoding each block could include encoding according to an inner code, wherein the inner code comprises an alphabet consisting of {adenine (A), cytosine (C), guanine (G), and thymine (T)}.

In various embodiments, each unique marker could be of the form $M=(AC)^l\|H(TG)^l$, where $l=25 \log n$.

In example embodiments, the encoded blocks could include approximately 50% guanine and cytosine content.

In some embodiments, encoding each block could include encoding each block according to a Hamming encoding with a relative Hamming distance.

In some embodiments, the method 300 could additionally include partitioning each block into a plurality of subblocks and inserting a second level of markers between each subblock. In such scenarios, the second level of markers may be different than the unique markers.

Figure 4:
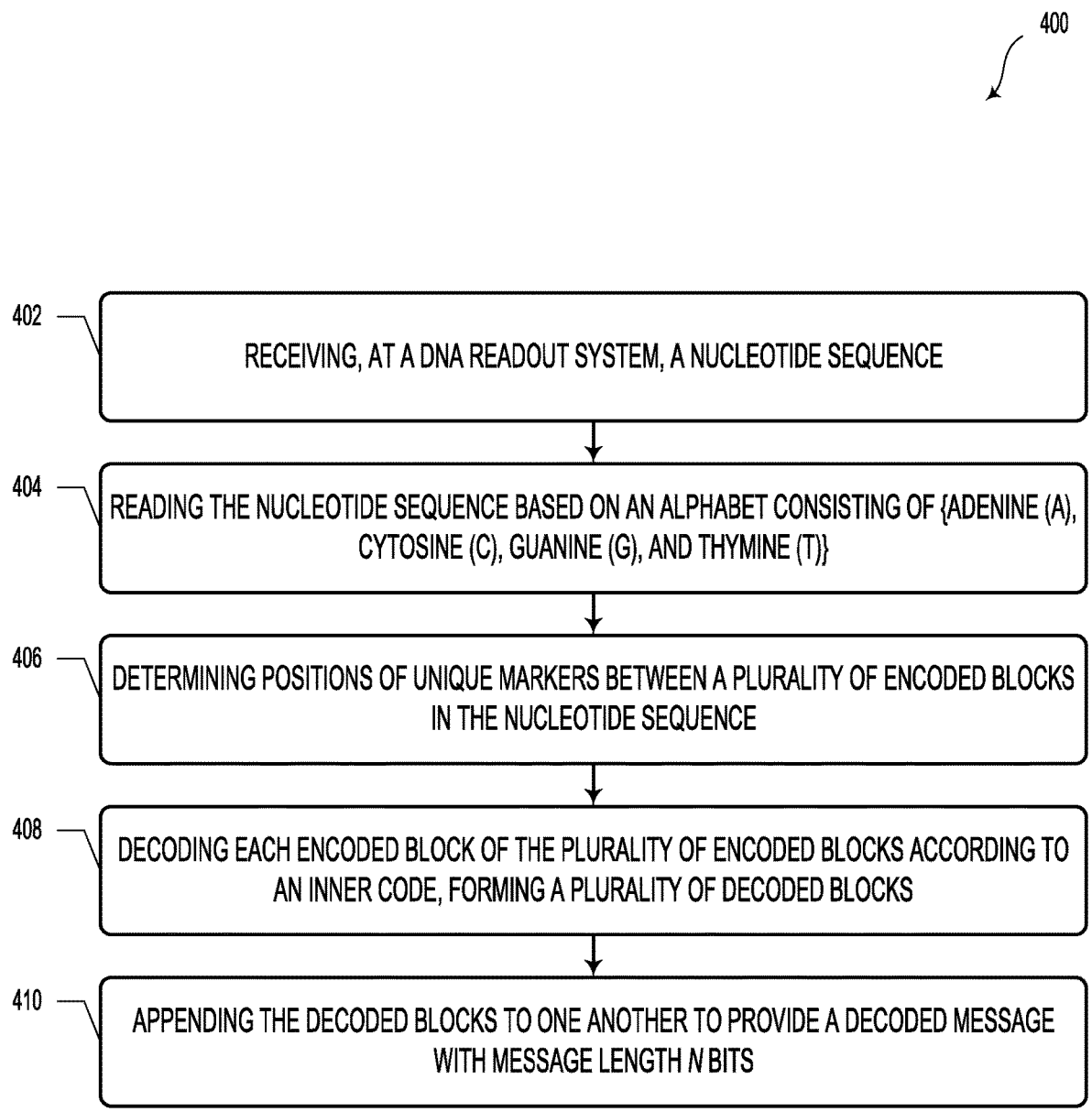
FIG. 4 illustrates a method, according to an example embodiment.

FIG. 4 illustrates a method 400, according to an example embodiment. It will be understood that the method 400 may include fewer or more steps or blocks than those expressly illustrated or otherwise disclosed herein. Furthermore, respective steps or blocks of method 400 may be performed in any order and each step or block may be performed one or more times. In some embodiments, some or all of the blocks or steps of method 400 may be carried out by a DNA-based readout system (e.g., DNA-based readout system 200). It will be understood that other scenarios are possible and contemplated within the context of the present disclosure.

Block 402 includes receiving, at a DNA readout system, a nucleotide sequence (e.g., nucleotide sequence 240).

Block 404 includes reading the nucleotide sequence based on an alphabet consisting of {adenine (A), cytosine (C), guanine (G), and thymine (T)}.

Block 406 includes determining positions of unique markers between a plurality of encoded blocks in the nucleotide sequence.

Block 408 includes decoding each encoded block of the plurality of encoded blocks according to an inner code, forming a plurality of decoded blocks.

Block 410 includes appending the decoded blocks to one another to provide a decoded message (e.g., decoded message 230) with message length n bits.

In some embodiments, each unique marker could be of the form $M=(AC)^l \| (TG)^l$, where $l=25 \log n$.

In various embodiments, the encoded blocks consist of approximately 50% guanine and cytosine content.

In example embodiments, encoding each block could include encoding each block according to a Hamming encoding with a relative Hamming distance.

The particular arrangements shown in the Figures should not be viewed as limiting. It should be understood that other embodiments may include more or less of each element shown in a given Figure. Further, some of the illustrated elements may be combined or omitted. Yet further, an illustrative embodiment may include elements that are not illustrated in the Figures.

A step or block that represents a processing of information can correspond to circuitry that can be configured to perform the specific logical functions of a herein-described method or technique. Alternatively or additionally, a step or block that represents a processing of information can correspond to a module, a segment, a physical computer (e.g., a field programmable gate array (FPGA) or application-specific integrated circuit (ASIC)), or a portion of program code (including related data). The program code can include one or more instructions executable by a processor for implementing specific logical functions or actions in the method or technique. The program code and/or related data can be stored on any type of computer readable medium such as a storage device including a disk, hard drive, or other storage medium.

The computer readable medium can also include non-transitory computer readable media such as computer-readable media that store data for short periods of time like register memory, processor cache, and random access memory (RAM). The computer readable media can also include non-transitory computer readable media that store program code and/or data for longer periods of time. Thus, the computer readable media may include secondary or persistent long term storage, like read only memory (ROM), optical or magnetic disks, compact-disc read only memory (CD-ROM), for example. The computer readable media can also be any other volatile or non volatile storage systems. A computer readable medium can be considered a computer readable storage medium, for example, or a tangible storage device.

While various examples and embodiments have been disclosed, other examples and embodiments will be apparent to those skilled in the art. The various disclosed examples and embodiments are for purposes of illustration and are not intended to be limiting, with the true scope being indicated by the following claims.

What is claimed is:

1. A method, comprising:
   partitioning a message having a message length n bits into a plurality of blocks with a maximum block length of $O(\log^2 n)$;
   encoding each block to provide a plurality of encoded blocks;
   inserting unique markers between the encoded blocks so as to form an encoded message, wherein the markers each have a minimum marker length $O(\log n)$; and
   synthesizing a DNA having a nucleotide sequence based on the encoded message.

2. The method of claim 1, wherein encoding each block comprises encoding according to an inner code, wherein the inner code comprises an alphabet consisting of adenine (A), cytosine (C), guanine (G), and thymine (T).

3. The method of claim 2, wherein each unique marker is of the form $M=(AC)^l \| (TG)^l$, where $l=25 \log n$.

4. The method of claim 2, wherein the encoded blocks consist of 50% guanine and cytosine content.

5. The method of claim 1, wherein encoding each block comprises encoding each block according to a Hamming encoding with a relative Hamming distance.

6. The method of claim 1, further comprising:
   further partitioning each block into a plurality of sub-blocks; and
   inserting a second level of markers between each sub-block, wherein the second level of markers is different than the unique markers.

7. A DNA-based data storage system comprising:
   a DNA synthesizer; and
   a controller configured to carry out operations, the operations including:
      partitioning a message having a message length n bits into a plurality of blocks with a maximum block length of $O(\log^2 n)$;
      encoding each block to provide a plurality of encoded blocks;
      inserting unique markers between the encoded blocks so as to form an encoded message, wherein the markers each have a minimum marker length $O(\log n)$; and
      informing the DNA synthesizer to synthesize a nucleotide sequence based on the encoded message.

8. The DNA-based data storage system of claim 7, wherein encoding each block comprises encoding according to an inner code, wherein the inner code comprises an alphabet consisting of adenine (A), cytosine (C), guanine (G), and thymine (T).

9. The DNA-based data storage system of claim 8, wherein each unique marker is of the form $M=(AC)^l \| (TG)^l$, where $l=25 \log n$.

10. The DNA-based data storage system of claim 8, wherein the encoded blocks consist of 50% guanine and cytosine content.

11. The DNA-based data storage system of claim 7, wherein encoding each block comprises encoding each block according to a Hamming encoding with a relative Hamming distance.

12. The DNA-based data storage system of claim 7, wherein the operations further comprise:
   further partitioning each block into a plurality of sub-blocks; and
   inserting a second level of markers between each sub-block, wherein the second level of markers is different than the unique markers.

* * * * *